(12) United States Patent
Joung et al.

(10) Patent No.: US 10,760,064 B2
(45) Date of Patent: *Sep. 1, 2020

(54) RNA-GUIDED TARGETING OF GENETIC AND EPIGENOMIC REGULATORY PROTEINS TO SPECIFIC GENOMIC LOCI

(71) Applicant: The General Hospital Corporation, Boston, MA (US)

(72) Inventors: J. Keith Joung, Winchester, MA (US); Morgan Maeder, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/211,117

(22) Filed: Mar. 14, 2014

(65) Prior Publication Data

US 2014/0377868 A1    Dec. 25, 2014

Related U.S. Application Data

(60) Provisional application No. 61/799,647, filed on Mar. 15, 2013.

(51) Int. Cl.
| | |
|---|---|
| C12N 15/85 | (2006.01) |
| C12N 15/11 | (2006.01) |
| C12N 15/31 | (2006.01) |
| C12N 15/62 | (2006.01) |
| C12N 15/52 | (2006.01) |
| C12N 9/22 | (2006.01) |
| C07K 14/315 | (2006.01) |
| C07K 14/47 | (2006.01) |
| C12N 15/63 | (2006.01) |
| C12N 15/113 | (2010.01) |

(52) U.S. Cl.
CPC ............ *C12N 9/22* (2013.01); *C07K 14/4705* (2013.01); *C12N 15/1136* (2013.01); *C12N 15/63* (2013.01); *C07K 2319/40* (2013.01); *C07K 2319/43* (2013.01); *C07K 2319/80* (2013.01); *C12N 2310/20* (2017.05); *C12N 2310/318* (2013.01); *C12N 2310/3231* (2013.01); *C12N 2310/3341* (2013.01)

(58) Field of Classification Search
None
See application file for complete search history.

(56) References Cited

U.S. PATENT DOCUMENTS

| | | | |
|---|---|---|---|
| 4,603,044 A | 7/1986 | Geho et al. | |
| 4,957,773 A | 9/1990 | Spencer et al. | |
| 5,436,150 A | 7/1995 | Srinivasan | |
| 6,007,988 A | 12/1999 | Choo et al. | |
| 6,013,453 A | 1/2000 | Choo et al. | |
| 6,503,717 B2 | 1/2003 | Case et al. | |
| 6,511,808 B2 | 1/2003 | Wolffe et al. | |
| 7,021,555 B2 | 4/2006 | Bagnall | |
| 7,220,719 B2 | 5/2007 | Case | |
| 7,914,796 B2 | 3/2011 | Miller et al. | |
| 7,919,277 B2 | 4/2011 | Russell et al. | |
| 8,034,598 B2 | 10/2011 | Miller | |
| 8,071,370 B2 | 12/2011 | Wolffe | |
| 8,252,535 B2 | 8/2012 | Biekle et al. | |
| 8,282,920 B2 | 10/2012 | Heo et al. | |
| 8,361,725 B2 | 1/2013 | Russell et al. | |
| 8,697,359 B1 | 4/2014 | Zhang | |
| 8,771,986 B2 | 7/2014 | Miller | |
| 8,865,406 B2 | 10/2014 | Zhang et al. | |
| 8,962,281 B2 | 2/2015 | Doyon | |
| 8,993,233 B2 | 3/2015 | Zhang et al. | |
| 9,023,649 B2 | 5/2015 | Mali et al. | |
| 9,074,199 B1 | 7/2015 | Chavez et al. | |
| 9,322,037 B2 | 4/2016 | Liu et al. | |
| 9,771,601 B2 | 9/2017 | May et al. | |
| 9,885,033 B2 | 2/2018 | Joung | |
| 9,926,546 B2 | 3/2018 | Joung et al. | |
| 2002/0160940 A1 | 10/2002 | Case et al. | |
| 2002/0164575 A1 | 11/2002 | Case et al. | |
| 2005/0214851 A1 | 9/2005 | Arts et al. | |
| 2006/0199190 A1 | 9/2006 | Russell et al. | |
| 2007/0020627 A1 | 1/2007 | Barbas, III | |
| 2008/0124725 A1 | 5/2008 | Barrangou et al. | |
| 2008/0193470 A1 | 8/2008 | Masignani et al. | |
| 2010/0034924 A1 | 2/2010 | Fremaux et al. | |
| 2010/0055793 A1 | 3/2010 | Chandrasegaran | |
| 2010/0076057 A1 | 3/2010 | Sontheimer et al. | |
| 2010/0093617 A1 | 4/2010 | Barrangou et al. | |
| 2010/0104690 A1 | 4/2010 | Barrangou et al. | |
| 2010/0120043 A1 | 5/2010 | Sood et al. | |
| 2010/0183559 A1 | 7/2010 | Van Sinderen et al. | |
| 2010/0184624 A1 | 7/2010 | Samuel et al. | |

(Continued)

FOREIGN PATENT DOCUMENTS

| | | |
|---|---|---|
| CN | 103224947 | 7/2013 |
| CN | 103233028 | 8/2013 |

(Continued)

OTHER PUBLICATIONS

Sanjana et al, A transcription activator-like effector toolbox for genome engineering, Nature Protocols, 2012, p. 171-192.*
Jinek et al, Supplementary Materials for A Programmable Dual-RNA-Guided DNA Endonuclease in Adaptive Bacterial Immunity, Science Express, 2012, pp. 1-37.*
Duodna and Charpentier, The new frontier of genome engineering with CRISPR-Cas9, Science Nov. 28, 2014: vol. 346, Issue 6213, pp. 1258096(1)-1258096(9).*
Gilbert et al, CRISPR-Mediated Modular RNA-Guided Regulation of Transcfription in Eukaryotes, Cell, 2013, pp. 442-451.*
Qi et al, Repurposing CRISPR as an RNA-Guided Platform for Sequence-Specific Control of Gene Expression, Cell 152, 1173-1183, Feb. 28, 2013.*

(Continued)

*Primary Examiner* — Maria Marvich
(74) *Attorney, Agent, or Firm* — Fish & Richardson P.C.

(57) ABSTRACT

Methods and constructs for RNA-guided targeting of transcriptional activators to specific genomic loci.

20 Claims, 14 Drawing Sheets

Specification includes a Sequence Listing.

(56) References Cited

U.S. PATENT DOCUMENTS

| | | |
|---|---|---|
| 2010/0209998 A1 | 8/2010 | Attwood et al. |
| 2010/0209999 A1 | 8/2010 | Altermann et al. |
| 2010/0221185 A1 | 9/2010 | Altermann et al. |
| 2010/0311061 A1 | 12/2010 | Korlach et al. |
| 2010/0317116 A1 | 12/2010 | Flusberg et al. |
| 2011/0002889 A1 | 1/2011 | Barrangou et al. |
| 2011/0092381 A1 | 4/2011 | Sood et al. |
| 2011/0143348 A1 | 6/2011 | Tomigahara et al. |
| 2011/0150852 A1 | 6/2011 | Chambaud et al. |
| 2011/0171647 A1 | 7/2011 | Tomigahara et al. |
| 2011/0189674 A1 | 8/2011 | Tomigahara et al. |
| 2011/0189776 A1 | 8/2011 | Terns et al. |
| 2011/0201007 A1 | 8/2011 | Waller et al. |
| 2011/0201118 A1 | 8/2011 | Yang et al. |
| 2011/0217739 A1 | 9/2011 | Terns et al. |
| 2011/0217791 A1 | 9/2011 | Tomigahara et al. |
| 2011/0223638 A1 | 9/2011 | Wiedenheft et al. |
| 2011/0236530 A1 | 9/2011 | Manoury et al. |
| 2011/0236894 A1 | 9/2011 | Rao et al. |
| 2011/0269119 A1 | 11/2011 | Hutchison et al. |
| 2011/0300528 A1 | 12/2011 | Jassim et al. |
| 2011/0300538 A1 | 12/2011 | Barrangou et al. |
| 2012/0027786 A1 | 2/2012 | Gupta et al. |
| 2012/0088676 A1 | 4/2012 | Weill et al. |
| 2012/0151635 A1 | 6/2012 | Coruzzi et al. |
| 2012/0214160 A1 | 8/2012 | Deng et al. |
| 2013/0011516 A1 | 1/2013 | Griffin et al. |
| 2013/0011828 A1 | 1/2013 | Barrangou et al. |
| 2013/0130248 A1 | 5/2013 | Haurwitz et al. |
| 2013/0145497 A1 | 6/2013 | Choi et al. |
| 2013/0150240 A1 | 6/2013 | Newman et al. |
| 2013/0158245 A1 | 6/2013 | Russell et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0330778 A1 | 12/2013 | Zeiner et al. |
| 2013/0337454 A1* | 12/2013 | Duchateau .............. C12N 9/22 435/6.12 |
| 2014/0068797 A1 | 3/2014 | Doudna et al. |
| 2014/0093941 A1 | 4/2014 | Terns et al. |
| 2014/0113376 A1 | 4/2014 | Sorek et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0356867 A1 | 12/2014 | Peter et al. |
| 2014/0356958 A1 | 12/2014 | Mali et al. |
| 2014/0357530 A1 | 12/2014 | Zhang et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056629 A1 | 2/2015 | Guthrie-Honea |
| 2015/0067922 A1 | 3/2015 | Yang et al. |
| 2015/0071899 A1 | 3/2015 | Liu et al. |
| 2015/0079681 A1 | 3/2015 | Zhang |
| 2015/0093473 A1 | 4/2015 | Barrangou et al. |
| 2015/0159174 A1 | 6/2015 | Frendeway et al. |
| 2015/0159175 A1 | 6/2015 | Frendeway et al. |
| 2015/0166969 A1 | 6/2015 | Takeuchi et al. |
| 2015/0167000 A1 | 6/2015 | Voytas et al. |
| 2015/0176064 A1 | 6/2015 | Fach et al. |
| 2015/0184139 A1 | 7/2015 | Zhang et al. |
| 2015/0191744 A1 | 7/2015 | Wolfe et al. |
| 2015/0203872 A1 | 7/2015 | Zhang |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0252358 A1 | 9/2015 | Maeder et al. |
| 2015/0291965 A1 | 10/2015 | Zhang et al. |
| 2015/0291966 A1 | 10/2015 | Zhang et al. |
| 2015/0315576 A1 | 11/2015 | Caliando et al. |
| 2015/0356239 A1 | 12/2015 | Zhang et al. |
| 2015/0376652 A1 | 12/2015 | Kuhn et al. |
| 2016/0010076 A1* | 1/2016 | Joung ..................... C12N 9/22 435/69.7 |
| 2016/0010147 A1 | 1/2016 | Heron |
| 2016/0017301 A1 | 1/2016 | Khalili et al. |
| 2016/0017366 A1 | 1/2016 | Chen et al. |
| 2016/0024510 A1 | 1/2016 | Bikard et al. |
| 2016/0024523 A1 | 1/2016 | Joung et al. |
| 2016/0024524 A1 | 1/2016 | Joung et al. |
| 2016/0024529 A1 | 1/2016 | Carstens et al. |
| 2016/0312198 A1* | 10/2016 | Joung .................. C12Y 301/00 |
| 2016/0362688 A1 | 12/2016 | May et al. |

FOREIGN PATENT DOCUMENTS

| | | |
|---|---|---|
| CN | 103343120 | 10/2013 |
| EP | 2325332 | 5/2011 |
| WO | WO 2003/072788 | 9/2003 |
| WO | WO 2004/099366 | 11/2004 |
| WO | WO 2007/014275 | 2/2007 |
| WO | WO 2007/025097 | 3/2007 |
| WO | WO 2008/108989 | 9/2008 |
| WO | WO 2010/054108 | 5/2010 |
| WO | WO 2011/017293 | 2/2011 |
| WO | WO 2011/143124 | 11/2011 |
| WO | WO 2012/093833 | 7/2012 |
| WO | WO 2012/164565 | 12/2012 |
| WO | WO 2013/012674 | 1/2013 |
| WO | WO 2013/098244 | 7/2013 |
| WO | WO 2013/141680 | 9/2013 |
| WO | WO 2013/142578 | 9/2013 |
| WO | WO 2013/169398 | 11/2013 |
| WO | WO 2013/176772 | 11/2013 |
| WO | WO 2014/0590255 | 4/2014 |
| WO | WO 2014/089290 | 6/2014 |
| WO | WO 2014/093622 | 6/2014 |
| WO | WO 2014/093655 | 6/2014 |
| WO | WO 2014/093712 | 6/2014 |
| WO | WO 2014/099744 | 6/2014 |
| WO | WO 2014/124284 | 8/2014 |
| WO | WO 2014/127287 | 8/2014 |
| WO | WO 2014/144288 | 9/2014 |

(56) References Cited

FOREIGN PATENT DOCUMENTS

| | | |
|---|---|---|
| WO | WO 2014/144592 | 9/2014 |
| WO | WO 2014/144761 | 9/2014 |
| WO | WO 2014/152432 | 9/2014 |
| WO | WO 2014/204578 | 12/2014 |
| WO | WO 2014/204724 | 12/2014 |
| WO | WO 2015/035162 | 3/2015 |
| WO | WO 2015/089364 | 6/2015 |
| WO | WO 2015/099850 | 7/2015 |
| WO | WO 2015/153940 | 10/2015 |
| WO | WO 2016/115355 | 6/2016 |

OTHER PUBLICATIONS

Lino et al, Delivering CRISPR: a review of the challenges and approaches, Drug Delivery 2018, vol. 25, No. 1, 1234-1257.*

Liu et al, Delivery strategies of the CRISPR-Cas9 gene-editing system for therapeutic applications, Journal of Controlled Release 266 (2017) 17-26.*

Al-Attar et al., "Clustered regularly interspaced short palindromic repeats (CRISPRs): the hallmark of an ingenious antiviral defense mechanism in prokaryotes," Biol Chem., Apr. 2011, 392:277-289.

Anonymous, "2013 Runners-Up. Genetic microsurgery for the masses," Science. Dec. 20, 2013;342(6165):1434-5.

Auer et al., "Highly efficient CRISPR/Cas9-mediated known-in in zebrafish by homology-independent DNA repair," Genome Res., 2014, 24:142-153.

Barker et al., "Increased DNA microarray hybridization specificity using sscDNA targets," BMC Genomics, Apr. 22, 2005, 6:57, 8 pages.

Baron-Benhamou et al., "Using the λn Peptide to Tether Proteins to RNAs," Methods Mole Biol., Jan. 2004, 257:135-153.

Barrangou et al., "CRISPR Provides Acquired Resistance Against Viruses in Prokaryotes," Science. Mar. 23, 2007;315(5819):1709-12.

Barrangou, "RNA-mediated programmable DNA cleavage," Nature Biotechnol., 2012, 30(9):836-838.

Bassett et al., "Highly efficient targeted mutagenesis of *Drosophila* with the CRISPR/Cas9 system," Cell Reports, 2013, 4:220-228.

Beerli et al., "Toward controlling gene expression at will: specific regulation of the erbB-2/HER-2 promoter by using polydactyl zinc finger proteins constructed from modular building blocks," PNAS USA, 1998, 95:14628-14633.

Belhaj et al., "Plant genome editing made easy: targeted mutagenesis in model and crop plants using the CRISPR/Cas system," Plant Methods, 2013, 9:39, 10 pages.

Bikard et al., "Programmable repression and activation of bacterial gene expression using an engineered CRISPR-Cas system," Nucleic Acid Res., Jun. 2013 41(15):7429-7437.

Bitinaite et al., "FokI dimerization is required for DNA cleavage," Proc. Natl. Acad. Sci. USA, 1998, 95:10570-10575.

Blackburn et al., "The CRISPR System-Keeping Zebrafish Gene Targeting Fresh," Zebrafish, 2013, 10(1):116-118.

Burgess, "A CRISPR genome-editing tool," Nature Reviews Genetics 14, 80-81 (Feb. 2013).

Carroll, "A CRISPR Approach to Gene Targeting," Molecular Therapy, 2012, 20(9):1658-1660.

Carroll, "Staying on target with CRISPR-Cas," Nat Biotechnol., 2013, 31(9):807-809.

Cathomen and Joung, "Zinc-finger nucleases: the next generation emerges," Mol. Ther., 2008, 16:1200-1207.

Chang et al., "Genome editing with RNA-guided Cas9 nuclease in zebrafish embryos," Cell Res., 2013, 23:465-472.

Chen et al., "Cut Site Selection by the Two Nuclease Domains of the Cas9 RNA-guided Endonuclease," J Biol Chem. May 9, 2014; 289(19):13284-94.

Chen et al., "Dynamic imaging of genomic loci in living human cells by an optimized CRISPR/Cas system," Cell, 2013, 155(7):1479-1491.

Chen et al., "Efficient genome editing in Caenorhabditis elegans by CRISPR-targeted homologous recombination," Nucleic Acids Res., 2013, 41(20):e193, 6 pages.

Cheng et al., "Multiplexed activation of endogenous genes by CRISPR-on, an RNA-guided transcriptional activator system," Cell Res., Oct. 2013, 23(10):1163-71.

Chiu et al., "Transgene-free genome editing in Caenorhabditis elegans using CRISPR-Cas," Genetics, Nov. 2013, 195(3):1167-71.

Cho et al., "Analysis of off-target effects of CRISPR/Cas-derived RNA-guided endonucleases and nickases," Genome Res., 2014, 24:132-141.

Cho et al., "Targeted genome engineering in human cells with the Cas9 RNA-guided endonuclease," Nat Biotechnol., 2013, 31:230-232.

Chylinski et al., "Classification and evolution of type II CRISPR-Cas systems," Nucleic Acids Res. 2014;42(10):6091-105.

Chylinski et al., "The tracrRNA and Cas9 families of type II CRISPR-Cas immunity systems," RNA Biol., 2013, 10(5):726-737.

Cong et al., "Multiplex genome engineering using CRISPR/Cas systems," Science, 2013, 339:819-823 (Author Manuscript).

Conklin, "Sculpting genomes with a hammer and chisel," Nature Methods, 2013, 10(9):839-840.

Cradick et al., "CRISPR/Cas9 systems targeting beta-globin and CCR5 genes have substantial off-target activity," Nucleic Acids Res., 2013, 41(20):9584-92.

de Souza, "RNA-guided gene editing," Nat Methods, Mar. 2013, 10(3):189.

Deltcheva et al., "CRISPR RNA maturation by trans-encoded small RNA and host factor Rnase III," Nature, 2011, 471(7340):602-607 (Author Manuscript).

Deveau et al., "Phage response to CRISPR-encoded resistance in *Streptococcus thermophilus*," J Bacteriol., Feb. 2008, 190(4):1390-400.

Dicarlo et al., "Genome engineering in *Saccharomyces cerevisiae* using CRISPR-Cas systems," Nucleic Acids Res., 2013, 41(7):4336-43.

Dickinson et al., "Engineering the Caenorhabditis elegans genome using Cas9-triggered homologous recombination," Nat Methods., Oct. 2013, 10(10):1028-34.

Ding et al., "Enhanced efficiency of human pluripotent stem cell genome editing through replacing TALENs with CRISPRs," Cell Stem Cell., Apr. 4, 2013, 12(4):393-4 (Author Manuscript).

Esvelt et al., "Orthogonal Cas9 proteins for RNA-guided gene regulation and editing," Nat Methods, Nov. 2013, 10(11):1116-21.

Fonfara et al., "Phylogeny of Cas9 determines functional exchangeability of dual-RNA and Cas9 among orthologous type II CRISPR-Cas systems." Nucleic Acids Res., Feb. 2014, 42(4):2577-90.

Friedland et al., "Heritable genome editing in C. elegans via a CRISPR-Cas9 system," Nature Methods 10(8): 741-743, 2013 (Author Manuscript).

Fu et al., "High-frequency off-target mutagenesis induced by CRISPR-Cas nucleases in human cells," Nat Biotechnol., 2013, 31:822-826 (Author Manuscript).

Gabriel et al., "An unbiased genome-wide analysis of zinc-finger nuclease specificity," Nat Biotechnol., 2011, 29:816-823.

Garneau et al., "The CRISPR/Cas bacterial immune system cleaves bacteriophage and plasmid DNA," Nature, Nov. 4, 2010, 468(7320):67-71.

Gasiunas and Siksnys, "RNA-dependent DNA endonuclease Cas9 of the CRISPR system: Holy Grail of genome editing?" Trends Microbiol., 2013, 21(11):562-567.

Gasiunas, "Cas9-crRNA ribonucleoprotein complex mediates specific DNA cleavage for adaptive immunity in bacteria," Proc Natl Acad Sci U S A, Sep. 25, 2012, 109(39):E2579-86.

Gilbert et al., "CRISPR-mediated modular RNA-guided regulation of transcription in eukaryotes," Cell, 2013, 154(2):442-51.

Gratz et al., "CRISPR/Cas9-mediated genome engineering and the promise of designer flies on demand," Fly (Austin), Oct.-Dec. 2013, 7(4):249-55.

Gratz et al., "Genome engineering of *Drosophila* with the CRISPR RNA-guided Cas9 nuclease," Genetics, 2013, 194(4):1029-35.

(56) References Cited

OTHER PUBLICATIONS

Guilinger et al., "Fusion of catalytically inactive Cas9 to FokI nuclease improves the specificity of genome modification," Nat Biotechnol., Apr. 2014, 32(6):577-583.
Hale et al., "Essential features and rational design of CRISPR RNAs that function with the Cas RAMP module complex to cleave RNAs," Mol Cell., 2012, 45(3):292-302 (Author Manuscript).
Hockemeyer et al., "Genetic engineering of human ES and iPS cells using TALE nucleases," Nat Biotechnol., 2011, 29:731-734 (Author Manuscript).
Horii et al., "Generation of an ICF Syndrome Model by Efficient Genome Editing of Human Induced Pluripotent Stem Cells using the CRISPR System," Int J Mol Sci., 2013, 14:19774-19781.
Horvath and Barrangou, "CRISPR/Cas, the immune system of bacteria and archaea," Science, 2010, 327:167-170.
Hou et al., "Efficient genome engineering in human pluripotent stem cells using Cas9 from Neisseria meningitidis," Proc Natl Acad Sci U S A, Sep. 24, 2013, 110(39):15644-9.
Hsu et al., "DNA targeting specificity of RNA-guided Cas9 nucleases," Nat Biotechnol., 2013, 31:827-832.
Hsu et al., "Development and Applications of CRISPR-Cas9 for Genome Engineering," Cell, 2014, 157(6): 1262-1278.
Hwang et al., "Efficient In Vivo Genome Editing Using RNA-Guided Nucleases," Nat Biotechnol., 2013, 31:227-229 (Author Manuscript).
Hwang et al., "Heritable and Precise Zebrafish Genome Editing Using a CRISPR-Cas System," PLoS One, 2013, 8(7):e68708, 9 pages.
Ishino et al., "Nucleotide sequence of the iap gene, responsible for alkaline phosphatase isozyme conversion in *Escherichia coli*, and identification of the gene product," J Bacteriol., Dec. 1987, 169(12):5429-33.
Iyer et al., "Prediction of novel families of enzymes involved in oxidative and other complex modifications of bases in nucleic acids," Cell Cycle, Jun. 1, 2009, 8(11):1698-710.
Jansen et al., "Identification of genes that are associated with DNA repeats in prokaryotes," Mol Microbiol., Mar. 2002, 43(6):1565-75.
Jiang et al., "CRISPR-assisted editing of bacterial genomes," Nat Biotechnol., 2013, 31:233-239 (Author Manuscript).
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 Endonucleases Reveal RNA-Mediated Conformational Activation," Science. Mar. 14, 2014; 343(6176):1247997.
Karvelis et al., "crRNA and tracrRNA guide Cas9-mediated DNA interference in *Streptococcus thermophilus*," RNA Biol., 2013, 10(5):841-851.
Katic and Großhans, "Targeted heritable mutation and gene conversion by Cas9-CRISPR in Caenorhabditis elegans," Genetics, Nov. 2013, 195(3):1173-6.
Keryer-Bibens et al., "Tethering of proteins to RNAs by bacteriophage proteins," Biol Cell, 2008, 100:125-138.
Kim and Kim, "A guide to genome engineering with programmable nucleases," Nature Rev Genetics 15, 321-334 (2014).
Kim et al., "Highly efficient RNA-guided genome editing in human cells via delivery of purified Cas9 ribonucleoproteins," Genome Res. Jun. 2014; 24(6):1012-9.
Koike-Yusa et al., "Genome-wide recessive genetic screening in mammalian cells with a lentiviral CRISPR-guide RNA library," Nat Biotechnol., Mar. 2014, 32(3):267-73.
Kondo and Ueda, "Highly improved gene targeting by germline-specific Cas9 expression in *Drosophila*," Genetics, Nov. 2013, 195(3):715-21.
Konermann et al., "Optical control of mammalian endogenous transcription and epigenetic states," Nature. Aug. 22, 2013; 500(7463):472-6. (Author Manuscript).
Li et al., "Heritable gene targeting in the mouse and rat using a CRISPR-Cas system," Nat Biotechnol, Aug. 2013, 31(8):681-3.

Li et al., "Simultaneous generation and germline transmission of multiple gene mutations in rat using CRISPR-Cas systems," Nat Biotechnol., Aug. 2013, 31(8):684-6.
Li et al., "Tal nucleases (TALNs): hybrid proteins composed of TAL effectors and FokI DNA-cleavage domain," Nucleic Acids Res., 2011, 39(1): 359-372.
Lo et al., "Precise and Heritable Genome Editing in Evolutionarily Diverse Nematodes Using TALENs and CRISPR/Cas9 to Engineer Insertions and Delections," Genetics, 2013, 195:331-348.
Maeder et al., "CRISPR RNA-guided activation of endogenous human genes," Nat Methods, 2013, 10:977-979 (Author Manuscript).
Maeder et al., "Rapid 'open-source' engineering of customized zinc-finger nucleases for highly efficient gene modification," Mol Cell, 2008, 31(2):294-301.
Makarova et al., "A putative RNA-interference-based immune system in prokaryotes: computational analysis of the predicted enzymatic machinery, functional analogies with eukaryotic RNAi, and hypothetical mechanisms of action," Biol Direct. Mar. 16, 2006;1:7, 26 pages.
Makarova et al., "Evolution and classification of the CRISPR-Cas systems," Nat. Rev. Microbiol., 2011, 9(6):467-77 (Author Manuscript).
Makarova et al., "Unification of Cas protein families and a simple scenario for the origin and evolution of CRISPR-Cas systems," Biol Direct. Jul. 14, 2011;6:38, 27 pages.
Mali et al., "Cas9 as a versatile tool for engineering biology," Nature Methods, 2013, 10(10):957-963.
Mali et al., "CAS9 transcriptional activators for target specificity screening and paired nickases for cooperative genome engineering," Nat Biotechnol., 2013, 31:833-838.
Mali et al., "RNA-guided human genome engineering via Cas9," Science, 2013, 339:823-826 (Author Manuscript).
Marraffini and Sontheimer, "CRISPR Interference Limits Horizontal Gene Transfer in Staphylococci by Targeting DNA," Sci., 2008, 322(5909):1843-1845.
Marraffini and Sontheimer, "Self vs. non-self discrimination during CRISPR RNA-directed immunity," Nature, 2010, 463(7280):568-571 (Author Manuscript).
Mashiko et al., "Generation of mutant mice by pronuclear injection of circular plasmid expressing Cas9 and single guided RNA," Sci Reports, 2013, 3(3355):1-6.
McGarty, "CRISPRs and Cancer," White Paper No. 111, Apr. 2014, 22 pages.
Miller et al., "An improved zinc-finger nuclease architecture for highly specific genome editing," Nat Biotechnol., 2007, 25:778-785.
Mojica et al., "Biological significance of a family of regularly spaced repeats in the genomes of Archaea, Bacteria and mitochondria," Mol Microbiol., Apr. 2000, 36(1):244-6.
Mussolino and Cathomen, "RNA guides genome engineering," Nat Biotechnol., 2013, 31(3):208-209.
Nishimasu et al., "Crystal structure of Cas9 in complex with guide RNA and target DNA," Cell, 2014, 156:935-949.
Niu et al., "Generation of gene-modified cynomolgus monkey via Cas9/RNA-mediated gene targeting in one-cell embryos," Cell, 2014, 156:836-843.
Pattanayak et al., "High-throughput profiling of off-target DNA cleavage reveals RNA-programmed Cas9 nuclease specificity," Nat Biotechnol., 2013, 31:839-843 (Author Manuscript).
Pattanayak et al., "Revealing off-target cleavage specificities of zinc-finger nucleases by in vitro selection," Nat Methods, 2011, 8:765-770 (Author Manuscript).
Perez et al., "Establishment of HIV-1 resistance in CD4+ T cells by genome editing using zinc-finger nucleases," Nat Biotechnol., 2008, 26:808-816 (Author Manuscript).
Perez-Pinera et al., "RNA-guided gene activation by CRISPR-Cas9-based transcription factors," Nat Methods, 2013, 10(10):973-976 (Author Manuscript).
Puchta and Fauser et al., "Synthetic nucleases for genome engineering in plants: prospects for a bright future," Plant J. Jun. 2014; 78(5):727-41.

(56) References Cited

OTHER PUBLICATIONS

Qi et al., "Repurposing CRISPR as an RNA-Guided Platform for Sequence-Specific Control of Gene Expression," Cell, Feb. 2013, 152:1173-1183.
Ramakrishna et al., "Gene disruption by cell-penetrating peptide-mediated delivery of Cas9 protein and guide RNA," Genome Res. Jun. 2014; 24(6): 1020-1027.
Ramakrishna et al., "Surrogate reporter-based enrichment of cells containing RNA-guided Cas9 nuclease-induced mutations," Nat Commun. Feb. 26, 2014; 5:3378.
Ramalingam et al., "A CRISPR way to engineer the human genome," Genome Biol., 2013, 14(2):107, 4 pages.
Ran et al., "Double nicking by RNA-guided CRISPR Cas9 for enhanced genome editing specificity," Cell, 2013, 154:1380-1389.
Ran et al., "Genome engineering using the CRISPR-Cas9 system," Nature Protocols, 2013, 8(11):2281-2308.
Ren et al., "Optimized gene editing technology for *Drosophila melanogaster* using germ line-specific Cas9," Proc Natl Acad Sci U S A, Nov. 19, 2013, 110(47):19012-7.
Reyon et al., "FLASH assembly of TALENs for high-throughput genome editing," Nat Biotech, 2012, 30:460-465 (Author Manuscript).
Rusk, "CRISPRs and epigenome editing," Nature Methods, 2014, 11(1):28.
Sander and Joung et al., "CRISPR-Cas systems for editing, regulating and targeting genomes," Nat Biotechnol., Apr. 2014, 32(4):347-55.
Sapranauskas et al., "The *Streptococcus thermophilus* CRISPR/Cas system provides immunity in *Escherichia coli*," Nucleic Acids Res., 2011, 39(21):9275-9282.
Schwank et al., "Functional repair of CFTR by CRISPR/Cas9 in intestinal stem cell organoids of cystic fibrosis patients," Cell Stem Cell, Dec. 5, 2013, 13(6):653-8.
Shen et al., "Efficient genome modification by CRISPR-Cas9 nickase with minimal off-target effects," Nat Methods, 2014, 11(4):399-402.
Shen et al., "Generation of gene-modified mice via Cas9/RNA-mediated gene targeting," Cell Res., 2013, 23(5):720-3.
Storrs, "A CRISPR Fore-Cas-t: a newcomer's guide to the hottest gene-editing tool on the block," The Scientist Magazine, Mar. 2014, 4 pages.
Sugimoto et al., "Thermodynamic parameters to predict stability of RNA/DNA hybrid duplexes," Biochemistry, 1995, 34:11211-11216.
Sugimoto et al., "Thermodynamics-structure relationship of single mismatches in RNA/DNA duplexes," Biochemistry, Sep. 19, 2000, 39(37):11270-81.
Szczepek et al., "Structure-based redesign of the dimerization interface reduces the toxicity of zinc-finger nucleases," Nat Biotechnol., 2007, 25:786-793.
Tan et al., "Efficient nonmeiotic allele introgression in livestock using custom endonucleases," Proc Natl Acad Sci U S A, Oct. 8, 2013, 110(41):16526-31.
Terns and Terns, "CRISPR-based adaptive immune systems," Curr Opin Microbiol., 2011, 14:321-327.
Tsai et al., "Dimeric CRISPR RNA-guided FokI nucleases for highly specific genome editing," Nat Biotechnol., Apr. 2014, 32(6):569-576.
Tzur et al., "Heritable Custom Genomic Modifications in Caenorhabditis elegans via a CRISPR-Cas9 System," Genetics, 2013, 195:1181-1185.
Waaigers et al., "CRISPR/Cas9-Targeted Mutagenesis in Caenorhabditis elegans," Genetics, 2013, 195:1187-1191.
Wang et al., "One-Step Generation of Mice Carrying Mutations in Multiple Genes by CRISPR/Cas-Mediated Genome Engineering," Cell, 2013, 153:910-918.
Wang et al., "The CRISPR/Cas system mediates efficient genome engineering in Bombyx mori," Cell Res., Dec. 2013, 23(12):1414-6.
Wiedenheft, "RNA-guided genetic silencing systems in bacteria and archaea," Nature 2012, 482:331-338.
Wu et al., "Correction of a genetic disease in mouse via use of CRISPR-Cas9," Cell Stem Cell., Dec. 5, 2013, 13(6):659-62.

Wu et al., "Genome-wide binding of the CRISPR endonuclease Cas9 in mammalian cells," Nat Biotechnol. Jul. 2014; 32(7):670-6.
Yang et al., "One-step generation of mice carrying reporter and conditional alleles by CRISPR/Cas-mediated genome engineering," Cell. Sep. 12, 2013; 154(6):1370-9.
Yin et al., "Genome editing with Cas9 in adult mice corrects a disease mutation and phenotype," Nature Biotechnology 32, 551-553 (2014).
Zhou et al., "High-throughput screening of a CRISPR/Cas9 library for functional genomics in human cells," Nature. May 22, 2014; 509(7501):487-91.
Alexopoulou et al., "The CMV early enhancer/chicken β actin (CAG) promoter can be used to drive transgene expression during the differentiation of murine embryonic stem cells into vascular progenitors," BMC Cell Biology, 2008, 9:2.
Anders et al., "Structural basis of PAM-dependent target DNA recognition by the Cas9 endonuclease," Nature, 2014, 513:569-573.
Arimondo et al., "Exploring the Cellular Activity of Camptothecin-Triple-Helix-Forming Oligonucleotide Conjugates," Mol. Cell. Biol., 26(1):324-33 (2006).
Arnould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et al., "Residues 1-254 of anthrax toxin lethal factor are sufficient to cause cellular uptake of fused polypeptides," J. Biol. Chem., Feb. 1993, 268:3334-41.
Bae et al., "Cas-OFFinder: a fast and versatile algorithm that searches for potential off-target sites of Cas9 RNA-guided endonucleases," Bioinformatics, 2014, 30:1473-1475.
Bae et al., "Human zinc fingers as building blocks in the construction of artificial transcription factors," Nat Biotechnol., 21(3):275-280, Epub Feb. 18, 2003.
Barrangou & May, "Unraveling the potential of CRISPR-Cas9 for gene therapy," Expert Opin. Biol. Ther., 2015, 15:311-314.
Beerli and Barbas, "Engineering polydactyl zinc-finger transcription factors," Nat Biotechnol., 20(2):135-141, Feb. 2002.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Blaese et al., "T lymphocyte-directed gene therapy for ADA-SCID: initial trial results after 4 years," Science, Oct. 1995, 270:475-480.
Boch et al., "Breaking the code of DNA binding specificity of TAL-type III effectors," Science, Dec. 11, 2009;326(5959):1509-12.
Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Burnett et al., "Conditional macrophage ablation in transgenic mice expressing a Fas-based suicide gene," J. Leukoc. Biol., Apr. 2004, 75(4):612-623.
Butler and Kadonaga, "The RNA polymerase II core promoter: a key component in the regulation of gene expression," Genes & Dev., 2002, 16:2583-2592.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carroll et al., "Design, construction and in vitro testing of zinc finger nucleases," Nat Protoc., 1(3):1329-1341, 2006.
Carroll, "Progress and prospects: zinc-finger nucleases as gene therapy agents," Gene Ther., 15(22):1463-1468, Epub Sep. 11, 2008.
Castellano et al., "Inducible recruitment of Cdc42 or WASP to a cell-surface receptor triggers actin polymerization and filopodium formation," Curr. Biol., 1999, 9(7): 351-360.

(56) References Cited

OTHER PUBLICATIONS

Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.HhaI Fused to Zinc Fingers," PLoS ONE, 7(9):E44852 pp. 1-11 (2012).
Chen & Zhao, "A highly sensitive selection method for directed evolution of homing endonucleases," Nucleic Acids Res., 2005, 33(18):e154.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Chim et al., "Methylation profiling in multiple myeloma," Leuk. Res., Apr. 2004, 28:379-85.
Choo and Klug, "Toward a code for the interactions of zinc fingers with DNA: selection of randomized fingers displayed on phage," Proc Natl Acad Sci U S A., 91(23):11163-11167, Nov. 8, 1994.
Christian et al., "Targeting DNA Double-Strand Breaks with TAL Effector Nucleases," Genetics, 2010, 186:757-761 (2010).
Clark-Curtiss and Curtiss, "[23] Analysis of recombinant DNA using *Escherichia coli* minicells," Methods in Enzymology, 1983, 101:347-362.
Colley et al., "Conversion of a Golgi Apparatus Sialyltransferase to a Secretory Protein by Replacement of the NH2-terminall Signal Anchor with a Signal Peptide," J. Biol. Chem., 1989, 264:17619-22.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
d'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
De Zhu, "The altered DNA methylation pattern and its implications in liver cancer," Cell. Res., 2005, 15:272-80.
Donnelly et al., "Targeted delivery of peptide epitopes to class I major histocompatibility molecules by a modified Pseudomonas exotoxin," PNAS, Apr. 1993, 90:3530-34.
Doudna and Charpentier, "Genome editing. The new frontier of genome engineering with CRISPR-Cas9," Science, Nov. 2014, 346:1258096, 11 pages.
Doyon et al., "Directed Evolution and Substrate Specificity Profile of Homing Endonuclease I-SceI," J. Am. Chem. Soc., 2006, 128:2477-2484.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dunbar et al., "Retrovirally Marked CD34-Enriched Peripheral Blood and Bone Marrow Cells Contribute to Long-Term Engraftment After Autologous Transplantation ," Blood, Jun. 1995, 85:3048-3057.
Eisenschmidt et al., "Developing a programmed restriction endonuclease for highly specific DNA cleavage," Nucleic Acids Res., 33(22):7039-47 (2005).
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elrod-Erickson et al., "High-resolution structures of variant Zif268-DNA complexes: implications for understanding zinc finger-DNA recognition," Structure, 6(4):451-464, Apr. 15, 1998.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
Fisher et al., "A scalable, fully automated process for construction of sequence-ready human exome targeted capture libraries," Genome Biol., 2011, 12-R1.
Freeman et al., "Inducible Prostate Intraepithelial Neoplasia with Reversible Hyperplasia in Conditional FGFR1-Expressing Mice," Cancer Res., Dec. 2003, 63(23):8256-8263.
Fu et al., "Improving CRISPR-Cas nuclease specificity using truncated guide RNAs," Nat. Biotechnol. Mar. 2014, 32:279-284.
Gagnon et al., "Efficient mutagenesis by Cas9 protein-mediated oligonucleotide insertion and large-scale assessment of single-guide RNAs," PLoS One, May 2014, 9, e98186.
Gao et al., "Hypermethylation of the RASSF1A gene in gliomas," Clin. Chim. Acta., Nov. 2004, 349:173-9.
Garcia-Bustos et al., "Nuclear protein localization," Biochim. Biophys. Acta, Mar. 1991, 1071:83-101.
Geibler et al., "Transcriptional Activators of Human Genes with Programmable DNA-Specificity," PLoS One, 6:e19509 (2011).
Gossen and Bujard, "Tight control of gene expression in mammalian cells by tetracycline-responsive promoters," Proc. Natl. Acad. Sci., Jun. 1992, 89:5547-5551.
Graef et al., "Proximity and orientation underlie signaling by the non-receptor tyrosine kinase ZAP70," Embo. J., 1997, 16(18):5618-5628.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Guilinger et al., "Broad specificity profiling of TALENs results in engineered nucleases with improved DNA-cleavage specificity," Nat. Methods, Apr. 2014, 11:429-435.
Guo et el., "Hydroxylation of 5-Methylcytosine by TET1 Promotes Active DNA Demethylation in the Adult Brain," Cell, 145:423-434 (2011).
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviral targeting of human breast cancer cells," PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.
Haurwitz et al., "Sequence- and Structure-Specific RNA Processing by a CRISPR Endonuclease," Science, Sep. 2010, 329(5997):1355-8.
Haurwitz, R. "The CRISPR endoribonuclease Csy4 utilizes unusual sequence and structure specific mechanisms to recognize and process crRNAs," Thesis. May 8, 2012 (May 8, 2012), University of California, Berkeley, pp. 1-120. Retrieved from the Internet:<http://escholarship.org/uc/item/0rh5940p> on Dec. 26, 2014 (Dec. 26, 2014). entire document.
He et al., "Tet-Mediated Formation of 5-Carboxylcytosine and Its Excision by TDG in Mammalian DNA," Science, 333:1303-1307 (2011).
Horvath et al., "Diversity, activity, and evolution of CRISPR loci in *Streptococcus thermophilus*," J. Bacteriol., Feb. 2008, 190:1401-1412.
Huang et al., "Heritable gene targeting in zebrafish using customized TALENs," Nat. Biotechnol., 29:699-700 (2011).
Isalan et al., "A rapid, generally applicable method to engineer zinc fingers illustrated by targeting the HIV-1 promoter," Nat. Biotechnol., 19(7):656-660, Jul. 2001.
Ito et al., "Tet proteins can convert 5-methylcytosine to 5-formylcytosine and 5-carboxylcytosine," Science, 333(6047):1300-1303, Sep. 2, 2011.
Iyer et al., Supplementary Material for "Prediction of novel families of enzymes involved in oxidative and other complex modifications of bases in nucleic acids," Cell Cycle, Jun. 1, 2009, 8(11):1698-710,

(56) References Cited

OTHER PUBLICATIONS

[retrived on Dec. 22, 2015]. Retrived from the Internet: URL <ftp://ftp.ncbi.nih.gov/pub/aravind/DONS/supplementary_material_DONS.html>.
Jamieson et al., "In vitro selection of zinc fingers with altered DNA-binding specificity," Biochemistry, 33(19):5689-5695, May 17, 1994.
Jiang et al., "Structural Biology. A Cas9-guide RNA complex preorganized for target DNA recognition," Science, Jun. 2015, 348:1477-1481.
Josephs et al., "Structure and specificity of the RNA-guided endonuclease Cas9 during DNA interrogation, target binding and cleavage," Nucleic Acids Res., Sep. 2015, 43:8924-8941.
Joung et al., "Reply to "Successful genome editing with modularly assembled zinc finger nucleases"," Nat. Methods, Jan. 2010, 7:91-92.
Joung and Sander, "TALENs: a widely applicable technology for targeted genome editing," Nat Rev Mol Cell Biol., 14(1):49-55, Epub Nov. 21, 2012.
Karmirantzou and Harnodrakas, "A Web-based classification system of DNA-binding protein families," Protein Eng. 14(7):465-472, Jul. 2001.
Kearns et al., "Recombinant adeno-associated virus (AAV-CFTR) vectors do not integrate in a site-specific fashion in an immortalized epithelial cell line," Gene Ther., Sep. 1996, 9:748-55.
Kiani et al., "Cas9 gRNA engineering for genome editing, activation and repression," Nat. Methods, 2015, 12:1051-1054.
Kim et al., "Genome editing with modularly assembled zinc-finger nucleases," Nat. Methods, 7(2):91-92, Feb. 2010.
Kim et al., "Targeted genome editing in human cells with zinc finger nucleases constructed via modular assembly," Genome Res., 19(7):1279-1288, Epub May 21, 2009.
Kleinstiver et al., "A unified genetic, computational and experimental framework identifies functionally relevant residues of the homing endonuclease I-Bmol," Nucleic Acids Res., 2010, 38:2411-2427.
Kleinstiver et al., "Engineered CRISPR-Cas9 nucleases with altered PAM specificities," Nature, Jul. 2015, 523(7561):481-5.
Klimpel et al., "Anthrax toxin protective antigen is activated by a cell surface protease with the sequence specificity and catalytic properties of furin," PNAS, Nov. 1992, 89:10277-81.
Klug, "Co-chairman's remarks: protein designs for the specific recognition of DNA," Gene, 135(1-2):83-92, Dec. 15, 1993.
Kumar et al., "DNA-Prot: identification of DNA binding proteins from protein sequence information using random forest," J Biomol Struct Dyn., 26(6):679-686, Jun. 2009.
Kumar et al., "Identification of DNA-binding proteins using support vector machines and evolutionary profiles," BMC Bioinformatics, 8:463, Nov. 27, 2007.
Kummerfeld and Teichmann, "DBD: a transcription factor prediction database," Nucleic Acids Res., 34 (Database issue): D74-D81, Jan. 1, 2006.
Kurmasheva et al., "Upstream CpG island methylation of the PAX3 gene in human rhabdomyosarcomas," Pediatr. Blood Cancer, Apr. 2005, 44:328-37.
Lea et al., "Aberrant p16 methylation is a biomarker for tobacco exposure in cervical squamous cell carcinogenesis," Am. J. Obstet. Gynecol., 2004, 190:674-9.
Lee et al., "Three-dimensional solution structure of a single zinc finger DNA-binding domain," Science., 245(4918):635-637, Aug. 11, 1989.
Li et al., "DNA methylation in prostate cancer," Biochim. Biophys. Acta., Sep. 2004, 1704:87-102.
Li et al., "Modularly assembled designer TAL effector nucleases for targeted gene knockout and gene replacement in eukaryotes," Nucleic Acids Res., 39(14):6315-6325, Epub Mar. 31, 2011.
Li et al., "Protein trans-splicing as a means for viral vector-mediated in vivo gene therapy," Hum Gene Ther., 19(9):958-964, Sep. 2008.

Lin et al., "CRISPR/Cas9 systems have off-target activity with insertions or deletions between target DNA and guide RNA sequences," Nucleic Acids Res., 2014, 42:7473-7485.
Lin et al., "iDNA-Prot: identification of DNA binding proteins using random forest with grey model," PLoS One., 6(9):e24756, Epub Sep. 15, 2011.
Liu et al., "Regulation of an Endogenous Locus Using a Panel of Designed Zinc Finger Proteins Targeted to Accessible Chromatin Regions," J. Biol. Chem., Apr. 2001, 276(14):11323-34.
Liu et al., "Validated zinc finger protein designs for all 16 GNN DNA triplet targets," J. Biol. Chem., 277(6):3850-3856, Epub Nov. 28, 2001.
Lund et al., "DNA Methylation Polymorphisms Precede Any Histological Sign of Atherosclerosis in Mice Lacking Apolipoprotein E," J. Biol. Chem., Jul. 2004, 279:29147-54.
Mabaera et al., "Developmental- and differentiation-specific patterns of human γ- and β-globin promoter DNA methylation," Blood, 110(4):1343-52 (2007).
Maeder et al., "Robust, synergistic regulation of human gene expression using TALE activators," Nat. Methods, 2013, 10:243-245.
Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.
Mahfouz et al., "De novo-engineered transcription activator-like effector (TALE) hybrid nuclease with novel DNA binding specificity creates double-strand breaks," Proc Natl Acad Sci U S A, 108:2623-2628 (2011).
Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.
Majumdar et al., "Targeted Gene Knock In and Sequence Modulation Mediated by a Psoralen-linked Triplex-forming Oligonucleotide," J Biol Chem., 283(17):11244-52 (2008).
Malech et al., "Prolonged production of NADPH oxidase-corrected granulocytes after gene therapy of chronic granulomatous disease," PNAS, Oct. 1997, 94:12133-38.
Mancini et al. "CpG methylation within the 5' regulatory region of the BRCA1 gene is tumor specific and includes a putative CREB binding site," Oncogene, 1998, 16:1161-9.
Mandell and Barbas et al., "Zinc Finger Tools: custom DNA-binding domains for transcription factors and nucleases," Nucleic Acids Res., 34(Web Server issue):W516-W523, Jul. 1, 2006.
Mendenhall et al., "Locus-specific editing of histone modifications at endogenous enhancers," Nat Biotechnol., 31(12):1133-1136, Epub Sep. 8, 2013.
Miller et al., "A TALE nuclease architecture for efficient genome editing," Nature Biotechnology, Feb. 2011, 29:143-148.
Miller et al., "Repetitive zinc-binding domains in the protein transcription factor IIIA from Xenopus oocytes," EMBO J., 4(6):1609-1614, Jun. 1985.
Miyazaki et al., "Expression vector system based on the chicken beta-actin promoter directs efficient production of interleukin-5," Gene, Jul. 1989, 79(2):269-77.
Mojica et al., "Short motif sequences determine the targets of the prokaryotic CRISPR defence system," Microbiology, 2009, 155:733-740.
Moore et al., "Design of polyzinc finger peptides with structured linkers," Proc Natl Acad Sci USA, Feb. 2001, 98:1432-1436.
Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.
Morbitzer et al., "Assembly of custom Tale-type DNA binding domains by modular cloning," Nucl Acids Res., 39:5790-5799 (2011).
Morrison, "Transformation in *Escherichia coli*: Cryogenic Preservation of Competent Cells," J. Bacteriol., Oct. 1977, 132:349-351.
Moscou and Bogdanove, "A simple cipher governs DNA recognition by TAL effectors," Science, 326(5959):1501, Dec. 11, 2009.

(56) References Cited

OTHER PUBLICATIONS

Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.
Needleman and Wunsch, "A General Method Applicable to the Search for Similarities in the Amino Acid Sequence of Two Proteins," J. Mol. Biol., 1970, 48:444-453.
Neering et al., "Transduction of Primitive Human Hematopoietic Cells With Recombinant Adenovirus Vectors," Blood, Aug. 1996, 88:1147-55.
Nissim et al., "Multiplexed and Programmable Regulation of Gene Networks with an Integrated RNA and CRISPR/Cas Toolkit in Human Cells," Molecular Cell, May 2014, 54:698-710.
Niwa et al., "Efficient selection for high-expression transfectants with a novel eukaryotic vector," Gene, 1991, 108(2):193-9.
Novak et al., "Functional Characterization of Protease-treated Bacillus anthracis Protective Antigen," J. Biol. Chem., Aug. 1992, 267:17186-93.
Oligino et al., "Drug inducible transgene expression in brain using a herpes simplex virus vector," Gene Ther., 1998, 5:491-496.
Palva et al., "Secretion of interferon by Bacillus subtilis," Gene, 1983, 22:229-235.
Pavletich and Pabo, "Zinc finger-DNA recognition: crystal structure of a Zif268-DNA complex at 2.1 A," Science, 252(5007):809-817, May 10, 1991.
Perelle et al., "Characterization of Clostridium perfringens Iota-Toxin Genes and Expression in *Eschenichia coli*," Infect. Immun., Dec. 1993, 61:5147-56.
Pingoud and Silva, "Precision genome surgery," Nat Biotechnol., 25(7):743-744, Jul. 2007.
Ramirez et al., "Unexpected failure rates for modular assembly of engineered zinc fingers," Nat Methods., 5(5):374-375, May 2008.
Ran et al., "In vivo genome editing using *Staphylococcus aureus* Cas9," Nature, 2015, 520:186-191.
Rebar and Pabo, "Zinc finger phage: affinity selection of fingers with new DNA-binding specificities," Science, 263(5147):671-673, Feb. 4, 1994.
Rendahl et al., "Regulation of gene expression in vivo following transduction by two separate rAAV vectors," Nat. Biotechnol., Aug. 1998, 16:757-761.
Ro et al., "Adenovirus-based short hairpin RNA vectors containing an EGFP marker and mouse U6, human H1, or human U6 promoter," BioTechniques, 2005, 38(4):625-627.
Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:230 12 pages (2010).
Rothman, "Mechanisms of intracellular protein transport," Nature, 372(6501):55-63, Nov. 3, 1994.
Sander et al., "In silico abstraction of zinc finger nuclease cleavage profiles reveals an expanded landscape of off-target sites," Nucleic Acids Res., 2013, 41:e181.
Sander et al., "ZiFiT (Zinc Finger Targeter): an updated zinc finger engineering tool," Nucleic Acids Res., 2010, 38:W462-468.
Sander et al., "Zinc Finger Targeter (ZiFiT): an engineered zinc finger/target site design tool," Nucleic Acids Res., 2007, 35:W599-605.
Sander et al., "Targeted gene disruption in somatic zebrafish cells using engineered TALENs," Nat. Biotechnol., 29:697-698 (2011).
Schleifman et al., "Triplex-mediated gene modification," Methods Mol. Biol., 435:175-190, 2008.
Scholze & Boch, "TAL effectors are remote controls for gene activation," J. Curr. Opin. Microbiol, 14:47-53 (2011).

Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA binding proteins," Biochemistry, 42(7):2137-2148, Feb. 25, 2003.
Shah et al., "Protospacer recognition motifs," RNA Biol., 2013, 10:891-899.
Sharma, "Schizophrenia, epigenetics and ligand-activated nuclear receptors: a framework for chromatin therapeutics," Schizophr. Res., Jan. 2005, 72:79-90.
Shmakov et al., "Discovery and Functional Characterization of Diverse Class 2 CRISPR-Cas Systems," Molecular Cell, 2015 60:385-397.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Sternberg et al., "Conformational control of DNA target cleavage by CRISPR-Cas9" Nature, 2015, 527:110-113.
Sternberg et al., "DNA interrogation by the CRISPR RNA-guided endonuclease Cas9," Nature, 2014, 507:62-67.
Sternberg et al., "Mechanism of substrate selection by a highly specific CRISPR endoribonuclease," RNA, 2012, 18:661-672.
Stoddard, "Homing endonuclease structure and function," Q. Rev. Biophys., 38(1): 49-95, Epub Dec. 9, 2005.
Szyf et al., "DNA methylation and breast cancer," Biochem. Pharmacol., Sep. 2004, 68:1187-97.
Tahiliani et al., "Conversion of 5-Methylcytosine to 5-Hydroxymethylcytosine in Mammalian DNA by MLL Partner TET1," Science, 324:930-935 (2009).
Tan et al., "Zinc-finger protein-targeted gene regulation: genomewide single-gene specificity," Proc Natl Acad Sci U S A., 100(21):11997-2002, Epub Sep. 26, 2003.
Tesson et al., "Knockout rats generated by embryo microinjection of TALENs," Nat. Biotechnol., 29:695-696 (2011).
Tjong and Zhou, "DISPLAR: an accurate method for predicting DNA-binding sites on protein surfaces," Nucleic Acids Res., 35(5):1465-1477, Epub Feb. 6, 2007.
Tsai et al., "GUIDE-Seq enables genome-wide profiling of off-target cleavage by CRISPR-Cas nucleases," Nat Biotechnol, Feb. 2015, 33:187-197.
Uhlmann et al., "Distinct methylation profiles of glioma subtypes," Int. J. Cancer, Aug. 2003, 106:52-9.
Ventura et al., "Cre-lox-regulated conditional RNA interference from transgenes," PNAS, Jul. 2004, 101:10380-10385.
Wagner et al., "Efficient and persistent gene transfer of AAV-CFTR in maxillary sinus," Lancet, Jun. 1998, 351:1702-1703.
Wang et al., "Positive and negative regulation of gene expression in eukaryotic cells with an inducible transcriptional regulator," Gene Ther., May 1997, 4:432-441.
Weber et al., "Assembly of Designer TAL Effectors by Golden Gate Cloning," PLoS One, 6:e19722 (2011).
Widschwendter and Jones, "DNA methylation and breast carcinogenesis," Oncogene, Aug. 2002, 21:5462-82.
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).

(56) References Cited

OTHER PUBLICATIONS

Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., 92(2):344-348, Jan. 17, 1995.
Wu et al., "Custom-designed zinc finger nucleases: what is next?" Cell Mol Life Sci., 64(22):2933-2944, Nov. 2007.
Xu et al., "Optimization of transcriptional regulatory elements for constructing plasmid vectors," Gene. Jul. 2001, 272(1-2):149-56.
Xu et al., "Genome-wide regulation of 5hmC, 5mC, and gene expression by Tet1 hydroxylase in mouse embryonic stem cells," Mol Cell., 42(4):451-464, Epub Apr. 21, 2011.
Yang et al., "Optimization of scarless human stem cell genome editing," Nucleic Acids Res., 2013,.41:9049-9061.
Zetsche et al., "Cpf1 Is a Single RNA-Guided Endonuclease of a Class 2 CRISPR-Cas System," Cell, 2015, 163:759-771.
Zhang et al., "Efficient construction of sequence-specific TAL effectors for modulating mammalian transcription," Nat Biotechnol., 29(2):149-153, Epub Jan. 19, 2011.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zitzewitz et al., "Probing the folding mechanism of a leucine zipper peptide by stopped-flA4:A48ism spectroscopy," Biochemistry, 34(39):12812-12819, Oct. 3, 1995.
Addgene 2016; CRISPR/Cas9 Guide on the web at addgene.org/CRISPR/guide/.
Appela., "Non-natural nucleic acids for synthetic biology", Current Opinion in Chemical Biology, Dec. 2009,13(5-6): 687-696.
Fu et al, Targeted genome editing in human cells using CRISPR/Cas nucleases and truncated guide RNAs, Methods in Enzymology, 546: 21-45.
Gaj et al., ZFN, TALEN, and CRISPR/Cas-based methods for genome engineering, Trends in Biotechnology, Jul. 2013, 31(7): 397-405.
Haft et al., "A Guild of 45 CRISPR-Associated (Cas) Protein Families and multiple CRISPER/cas Subtypes Exist in Prokaryotic Genomes," PLOS, 2005, 1(6):0474-0483.
Karkare and Bhatnagar, "Promising nucleic acid analogs and mimics: characteristic features and applications of PNA, LNA, and morpholino", Applied Microbiology and Biotechnology, May 2006, 71(5): 575-586.
Slaymaker et al. 2016; Rationally engineered Cas9 nucleases with improved specificity. Science 351(6268): 84-88.
Wolfe et al., "DNA recognition by Cys2His2 zinc finger proteins," Annu Rev Biophys Biomol Struct. 29:183-212 (2000).
Kleinstiver et al., "High-fidelity CR1SPR-Cas9 nucleases with no detectable genome-wide off-targets," Nature, Jan. 2016, 529: 490-495.
Kim et al., "Hybrid restriction enzymes: zinc finger fusions to Fok I cleavage domain," PNAS, Feb. 1996, 93: 1156-1160.
Melo et al., "eRNAs Are Required for p53-Dependent Enhancer Activity and Gene Transcription," Mol Cell, Feb. 2013, 49: 524-535.
Mino et al., "Efficient double-strand DNA cleavage by artificial zinc-finger nucleases composed of one zinc-finger protein and a single-chain FokI dimer," Journal of biotechnology, 2009, 140: 156-161.
Nielsen et al., "Interaction with members of the heterochromatin protein 1 (HP1) family and histone deacetylation are differentially involved in transcriptional silencing by members of the TIF1 family," EMBO J., 1999, 18: 6385-6395.
Qi et al., "Repurposing CRISPR as an RNA-Guided Platform for Sequence-Specific Control of Gene Expression," Cell, Feb. 2013, Supplemental Information, 152(5): 1173-1183.
Williams et al., "Tet1 and hydroxymethylcytosine in transcription and DNA methylation fidelity," Nature, May 2011, 473: 343-349.
Ma et al., "A Guide RNA Sequence Design Platform for the CRISPR/Cas9 System for Model Organism Genomes," BioMed Research International, 2013, 2013: 270805, 4 pages.
Farboud and Meyer, "Dramatic Enhancement of Genome Editing by CRISPR/Cas9 Through Improved Guide RNA Design," Genetics, 2015, 199:959-971.
Jiang et al., "RNA-guided editing of bacterial genomes using CRISPR-Cas systems," Nature Biotechnology, Mar. 2013, 31: 233-239.
Kleinstiver et al., "High-fidelity CR1SPR-Cas9 nucleases with no detectable genome-wide off target effects," Nature, Jan. 2016, 529: 490-495.
Ui-Tei et al., "Functional dissection of siRNA sequence by systematic DNA substitution: modified siRNA with a DNA seed arm is a powerful tool for mammalian gene silencing with significantly reduced off-target effect," Nucleic Acids Research, 2008, 36: 2136-2151.
EP Extended European Search Report in European Appln. No. 16842722.7, dated Jun. 7, 2019, 13 pages.
Extended European Search Report in Application No. 18208105.9, dated Jan. 15, 2019, 10 pages.
JP Office Action in Japanese Appln. No. 2016-502406, dated May 31, 2019, 24 pages (with English translation).
JP Office Action in Japanese Appln. No. 2016-502853, dated May 29, 2019, 7 pages (with English translation).
Office Action in Chinese Application No. 201480076396.6, dated Feb. 19, 2019, 16 pages (with English translation).
Office Action in Israeli Application No. 241671, dated Sep. 13, 2018, 8 pages (with English translation).
Office Action in Japanese Application No. 2016-502976, dated Apr. 2, 2019, 15 pages (with English translation).
Partial Supplementary Search report in European Application No. 16842722.7, dated Mar. 7, 2019, 13 pages.
Yin et al., "Partial DNA-guided Cas9 enables genome editing with reduced off-target activity," Nature Chemical Biology, Mar. 2018, 14(3)311-316.

* cited by examiner

FIG. 4 - Guide RNA expression vector sequence

```
GACGTCGCTAGCTGTACAAAAAAGCAGGCTTTAAAGGAACCAATTCAGTCGACTGGATCCGGTACCAAGG
TCGGGCAGGAAGAGGGCCTATTTCCCATGATTCCTTCATATTTGCATATACGATACAAGGCTGTTAGAGA
GATAATTAGAATTAATTTGACTGTAAACACAAAGATATTAGTACAAAATACGTGACGTAGAAAGTAATAA
TTTCTTGGGTAGTTTGCAGTTTTAAAATTATGTTTTAAAATGGACTATCATATGCTTACCGTAACTTGAA
AGTATTTCGATTTCTTGGCTTTATATATCTTGTGGAAAGGACGAAACACCNNNNNNNNNNNNNNNNNNNN
GTTTTAGAGCTAGAAATAGCAAGTTAAAATAAGGCTAGTCCGTTATCAACTTGAAAAAGTGGCACCGAGT
CGGTGCTTTTTTTAAGCTTGGGCCGCTCGAGGTACCTCTCTACATATGACATGTGAGCAAAAGGCCAGCA
AAAGGCCAGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGATACCTGTCCGCCTTTCTCCC
TTCGGGAAGCGTGGCGCTTTCTCATAGCTCACGCTGTAGGTATCTCAGTTCGGTGTAGGTCGTTCGCTCC
AAGCTGGGCTGTGTGCACGAACCCCCCGTTCAGCCCGACCGCTGCGCCTTATCCGGTAACTATCGTCTTG
AGTCCAACCCGGTAAGACACGACTTATCGCCACTGGCAGCAGCCACTGGTAACAGGATTAGCAGAGCGAG
GTATGTAGGCGGTGCTACAGAGTTCTTGAAGTGGTGGCCTAACTACGGCTACACTAGAAGAACAGTATTT
GGTATCTGCGCTCTGCTGAAGCCAGTTACCTTCGGAAAAAGAGTTGGTAGCTCTTGATCCGGCAAACAAA
CCACCGCTGGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTTAAATCAATCTAAA
GTATATATGAGTAAACTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATCAGCAATAAACC
AGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATCAAGGCGAGTTA
CATGATCCCCCATGTTGTGCAAAAAAGCGGTTAGCTCCTTCGGTCCTCCGATCGTTGTCAGAAGTAAGTT
GGCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGCT
CTTGCCCGGCGTCAATACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAATATTA
TTGAAGCATTTATCAGGGTTATTGTCTCATGAGCGGATACATATTTGAATGTATTTAGAAAAATAAACAA
ATAGGGGTTCCGCGCACATTTCCCCGAAAAGTGCCACCT   (SEQ ID NO:4)
```

FIG. 5 - CMV-T7-Cas9 D10A/H840A-3XFLAG-VP64:

ATATGCCAAGTACGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGATGCGGTTTTGGCAG
TACATCAATGGGCGTGGATAGCGGTTTGACTCACGGGGATTTCCAAGTCTCCACCCCATTGACGTCAATGGGAG
TTTGTTTTGGCACCAAAATCAACGGGACTTTCCAAAATGTCGTAACAACTCCGCCCCATTGACGCAAATGGGCG
GTAGGCGTGTACGGTGGGAGGTCTATATAAGCAGAGCTGGTTTAGTGAACCGTCAGATCCGCTAGAGATCCGC
GGCCGCTAATACGACTCACTATAGGGAGAGCCGCCACCATGGATAAGAAATACTCAATAGGCTTAGcTATCGGC
ACAAATAGCGTCGGATGGGCGGTGATCACTGATGAATATAAGGTTCCGTCTAAAAAGTTCAAGGTTCTGGGAA
ATACAGACCGCCACAGTATCAAAAAAAATCTTATAGGGGCTCTTTTATTTGACAGTGGAGAGACAGCGGAAGC
GACTCGTCTCAAACGGACAGCTCGTAGAAGGTATACACGTCGGAAGAATCGTATTTGTTATCTACAGGAGATTT
TTTCAAATGAGATGGCGAAAGTAGATGATAGTTTCTTTCATCGACTTGAAGAGTCTTTTTGGTGGAAGAAGAC
AAGAAGCATGAACGTCATCCTATTTTTGGAAATATAGTAGATGAAGTTGCTTATCATGAGAAATATCCAACTATC
TATCATCTGCGAAAAAAATTGGTAGATTCTACTGATAAAGCGGATTTGCGCTTAATCTATTTGGCCTTAGCGCAT
ATGATTAAGTTTCGTGGTCATTTTTTGATTGAGGGAGATTTAAATCCTGATAATAGTGATGTGGACAAACTATTT
ATCCAGTTGGTACAAACCTACAATCAATTATTTGAAGAAAACCCTATTAACGCAAGTGGAGTAGATGCTAAAGC
GATTCTTTCTGCACGATTGAGTAAATCAAGACGATTAGAAAATCTCATTGCTCAGCTCCCCGGTGAGAAGAAAA
ATGGCTTATTTGGGAATCTCATTGCTTTGTCATTGGGTTTGACCCCTAATTTTAAATCAAATTTTGATTGGCAGA
AGATGCTAAATTACAGCTTTCAAAAGATACTTACGATGATGATTTAGATAATTTATTGGCGCAAATTGGAGATC
AATATGCTGATTTGTTTTTGGCAGCTAAGAATTTATCAGATGCTATTTTACTTTCAGATATCCTAAGAGTAAATAC
TGAAATAACTAAGGCTCCCCTATCAGCTTCAATGATTAAACGCTACGATGAACATCATCAAGACTTGACTCTTTT
AAAAGCTTTAGTTCGACAACAACTTCCAGAAAAGTATAAAGAAATCTTTTTTGATCAATCAAAAAACGGATATG
CAGGTTATATTGATGGGGGAGCTAGCCAAGAAGAATTTTATAAATTTATCAAACCAATTTTAGAAAAAATGGAT
GGTACTGAGGAATTATTGGTGAAACTAAATCGTGAAGATTTGCTGCGCAAGCAACGGACCTTTGACAACGGCT
CTATTCCCCATCAAATTCACTTGGGTGAGCTGCATGCTATTTTGAGAAGACAAGAAGACTTTTATCCATTTTTAA
AAGACAATCGTGAGAAGATTGAAAAAATCTTGACTTTTCGAATTCCTTATTATGTTGGTCCATTGGCGCGTGGC
AATAGTCGTTTTGCATGGATGACTCGGAAGTCTGAAGAAACAATTACCCCATGGAATTTTGAAGAAGTTGTCGA
TAAAGGTGCTTCAGCTCAATCATTTATTGAACGCATGACAAACTTTGATAAAAATCTTCCAAATGAAAAAGTACT
ACCAAAACATAGTTTGCTTTATGAGTATTTTACGGTTTATAACGAATTGACAAAGGTCAAATATGTTACTGAAGG
AATGCGAAAACCAGCATTTCTTTCAGGTGAACAGAAGAAAGCCATTGTTGATTTACTCTTCAAAACAAATCGAA
AAGTAACCGTTAAGCAATTAAAAGAAGATTATTTCAAAAAAATAGAATGTTTTGATAGTGTTGAAATTTCAGGA
GTTGAAGATAGATTTAATGCTTCATTAGGTACCTACCATGATTTGCTAAAAATTATTAAAGATAAAGATTTTTTG
GATAATGAAGAAAATGAAGATATCTTAGAGGATATTGTTTTAACATTGACCTTATTTGAAGATAGGGAGATGAT
TGAGGAAAGACTTAAAACATATGCTCACCTCTTTGATGATAAGGTGATGAAACAGCTTAAACGTCGCCGTTATA
CTGGTTGGGGACGTTTGTCTCGAAAATTGATTAATGGTATTAGGGATAAGCAATCTGGCAAAACAATATTAGAT
TTTTTGAAATCAGATGGTTTTGCCAATCGCAATTTTATGCAGCTGATCCATGATGATAGTTTGACATTTAAAGAA
GACATTCAAAAAGCACAAGTGTCTGGACAAGGCGATAGTTTACATGAACATATTGCAAATTTAGCTGGTAGCCC
TGCTATTAAAAAAGGTATTTTACAGACTGTAAAAGTTGTTGATGAATTGGTCAAAGTAATGGGGCGGCATAAGC
CAGAAAATATCGTTATTGAAATGGCACGTGAAAATCAGACAACTCAAAAGGGCCAGAAAAATTCGCGAGAGCG
TATGAAACGAATCGAAGAAGGTATCAAAGAATTAGGAAGTCAGATTCTTAAAGAGCATCCTGTTGAAAATACTC
AATTGCAAAATGAAAAGCTCTATCTCTATTATCTCCAAAATGGAAGAGACATGTATGTGGACCAAGAATTAGAT
ATTAATCGTTTAAGTGATTATGATGTCGATgcCATTGTTCCACAAAGTTTCCTTAAAGACGATTCAATAGACAATA
AGGTCTTAACGCGTTCTGATAAAAATCGTGGTAAATCGGATAACGTTCCAAGTGAAGAAGTAGTCAAAAAGAT
GAAAAACTATTGGAGACAACTTCTAAACGCCAAGTTAATCACTCAACGTAAGTTTGATAATTTAACGAAAGCTG
AACGTGGAGGTTTGAGTGAACTTGATAAAGCTGGTTTTATCAAACGCCAATTGGTTGAAACTCGCCAAATCACT
AAGCATGTGGCACAAATTTTGGATAGTCGCATGAATACTAAATACGATGAAAATGATAAACTTATTCGAGAGGT

FIG. 5 (Continued) - CMV-T7-Cas9 D10A/H840A-3XFLAG-VP64:

```
TAAAGTGATTACCTTAAAATCTAAATTAGTTTCTGACTTCCGAAAAGATTTCCAATTCTATAAAGTACGTGAGAT
TAACAATTACCATCATGCCCATGATGCGTATCTAAATGCCGTCGTTGGAACTGCTTTGATTAAGAAATATCCAAA
ACTTGAATCGGAGTTTGTCTATGGTGATTATAAAGTTTATGATGTTCGTAAAATGATTGCTAAGTCTGAGCAAG
AAATAGGCAAAGCAACCGCAAAATATTTCTTTTACTCTAATATCATGAACTTCTTCAAAACAGAAATTACACTTG
CAAATGGAGAGATTCGCAAACGCCCTCTAATCGAAACTAATGGGGAAACTGGAGAAATTGTCTGGGATAAAGG
GCGAGATTTTGCCACAGTGCGCAAAGTATTGTCCATGCCCCAAGTCAATATTGTCAAGAAAACAGAAGTACAGA
CAGGCGGATTCTCCAAGGAGTCAATTTTACCAAAAAGAAATTCGGACAAGCTTATTGCTCGTAAAAAGACTGG
GATCCAAAAAAATATGGTGGTTTTGATAGTCCAACGGTAGCTTATTCAGTCCTAGTGGTTGCTAAGGTGGAAAA
AGGGAAATCGAAGAAGTTAAAATCCGTTAAAGAGTTACTAGGGATCACAATTATGGAAAGAAGTTCCTTTGAA
AAAAATCCGATTGACTTTTTAGAAGCTAAAGGATATAAGGAAGTTAAAAAAGACTTAATCATTAAACTACCTAA
ATATAGTCTTTTTGAGTTAGAAAACGGTCGTAAACGGATGCTGGCTAGTGCCGGAGAATTACAAAAAGGAAAT
GAGCTGGCTCTGCCAAGCAAATATGTGAATTTTTTATATTTAGCTAGTCATTATGAAAAGTTGAAGGGTAGTCC
AGAAGATAACGAACAAAAACAATTGTTTGTGGAGCAGCATAAGCATTATTTAGATGAGATTATTGAGCAAATCA
GTGAATTTTCTAAGCGTGTTATTTTAGCAGATGCCAATTTAGATAAAGTTCTTAGTGCATATAACAAACATAGAG
ACAAACCAATACGTGAACAAGCAGAAAATATTATTCATTTATTTACGTTGACGAATCTTGGAGCTCCCGCTGCTT
TTAAATATTTTGATACAACAATTGATCGTAAACGATATACGTCTACAAAAGAAGTTTTAGATGCCACTCTTATCC
ATCAATCCATCACTGGTCTTTATGAAACACGCATTGATTTGAGTCAGCTAGGAGGTGACGGTTCTCCCAAGAAG
AAGAGGAAAGTCTCGAGCGACTACAAAGACCATGACGGTGATTATAAAGATCATGACATCGATTACAAGGATG
ACGATGACAAGGctgcaggaggcggtggaagcGGGCGCGCCGACGCGCTGGACGATTTCGATCTCGACATGCTGGGT
TCTGATGCCCTCGATGACTTTGACCTGGATATGTTGGGAAGCGACGCATTGGATGACTTTGATCTGGACATGCT
CGGCTCCGATGCTCTGGACGATTTCGATCTCGATATGTTATAAccggtCATCATCACCATCACCATTGAGTTTAAA
CCCGCTGATCAGCCTCGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAATAGCAGGCATGCT
GGGGATGCGGTGGGCTCTATGGCTTCTGAGGCGGAAAGAACCAGCTGGGGCTCGATACCGTCGACCTCTAGCT
AGAGCTTGGCGTAATCATGGTCATAGCTGTTTCCTGTGTGAAATTGTTATCCGCTCACAATTCCACACAACATAC
GAGCCGGAAGCATAAAGTGTAAAGCCTAGGGTGCCTAATGAGTGAGCTAACTCACATTAATTGCGTTGCGCTC
ACTGCCCGCTTTCCAGTCGGGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGATACCTGTCCGCCTTTCT
CCTTCGGGAAGCGTGGCGCTTTCTCAATGCTCACGCTGTAGGTATCTCAGTTCGGTGTAGGTCGTTCGCTCCAA
GCTGGGCTGTGTGCACGAACCCCCCGTTCAGCCCGACCGCTGCGCCTTATCCGGTAACTATCGTCTTGAGTCCA
ACCCGGTAAGACACGACTTATCGCCACTGGCAGCAGCCACTGGTAACAGGATTAGCAGAGCGAGGTATGTAGG
CGGTGCTACAGAGTTCTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAGGATCTCAAGAAGATCCTTTGATCTTTTCTAC
GGGGTCTGACGCTCAGTGGAACGAAAACTCACGTTAAGGGATTTTGGTCATGAGATTATCAAAAGGATCTTC
ACCTAGATCCTTTTAAATTAAAAATGAAGTTTTAAATCAATCTAAAGTATATATGAGTAAACTTGGTCTGACAGT
TACCAATGCTTAATCAGTGAGGCACCTATCTCAGCGATCTGTCTATTTCGTTCATCCATAGTTGCCTGACTCCCG
TCGTGTAGATAACTACGATACGGGAGGGCTTACCATCTGGCCCCAGTGCTGCAATGATACCGCGAGACCCACG
CTCACCGGCTCCAGATTTATCAGCAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAGTAGTTCGCCAGTTAATAGTTTGCGC
AACGTTGTTGCCATTGCTACAGGCATCGTGGTGTCACGCTCGTCGTTTGGTATGGCTTCATTCAGCTCCGGTTCC
```

FIG. 5 (Continued) - CMV-T7-Cas9 D10A/H840A-3XFLAG-VP64:

```
CAACGATCAAGGCGAGTTACATGATCCCCCATGTTGTGCAAAAAAGCGGTTAGCTCCTTCGGTCCTCCGATCGT
TGTCAGAAGTAAGTTGGCCGCAGTGTTATCACTCATGGTTATGGCAGCACTGCATAATTCTCTTACTGTCATGCC
ATCCGTAAGATGCTTTTCTGTGACTGGTGAGTACTCAACCAAGTCATTCTGAGAATAGTGTATGCGGCGACCGA
GTTGCTCTTGCCCGGCGTCAATACGGGATAATACCGCGCCACATAGCAGAACTTTAAAAGTGCTCATCATTGGA
AAACGTTCTTCGGGGCGAAAACTCTCAAGGATCTTACCGCTGTTGAGATCCAGTTCGATGTAACCCACTCGTGC
ACCCAACTGATCTTCAGCATCTTTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCTTTTTCAATATTATTGAAGCATTT
ATCAGGGTTATTGTCTCATGAGCGGATACATATTTGAATGTATTTAGAAAAATAAACAAATAGGGGTTCCGCGC
ACATTTCCCCGAAAAGTGCCACCTGACGTCGACGGATCGGGAGATCGATCTCCCGATCCCCTAGGGTCGACTCT
CAGTACAATCTGCTCTGATGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATGAAGAATCTGCTTAGGGT
TAGGCGTTTTGCGCTGCTTCGCGATGTACGGGCCAGATATACGCGTTGACATTGATTATTGACTAGTTATTAATA
GTAATCAATTACGGGGTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCATAGTAACGCCAATAG
GGACTTTCCATTGACGTCAATGGGTGGACTATTTACGGTAAACTGCCCACTTGGCAGTACATCAAGTGTATCC
(SEQ ID NO:5)
```

FIG. 6 - MV-T7-Cas9 recoded D10A/H840A-3XFLAG-VP64

```
ATATGCCAAGTACGCCCCCTATTGACGTCAATGACGGTAAATGGCCCGCCTGGCATTATGCCCAGTACATGACC
TTATGGGACTTTCCTACTTGGCAGTACATCTACGTATTAGTCATCGCTATTACCATGGTGATGCGGTTTTGGCAG
TACATCAATGGGCGTGGATAGCGGTTTGACTCACGGGGATTTCCAAGTCTCCACCCCATTGACGTCAATGGGAG
TTTGTTTTGGCACCAAAATCAACGGGACTTTCCAAAATGTCGTAACAACTCCGCCCCATTGACGCAAATGGGCG
GTAGGCGTGTACGGTGGGAGGTCTATATAAGCAGAGCTGGTTTAGTGAACCGTCAGATCCGCTAGAGATCCGC
GGCCGCTAATACGACTCACTATAGGGAGAGCCGCCACCATGGATAAAAAGTATTCTATTGGTTTAGcCATCGGC
ACTAATTCCGTTGGATGGGCTGTCATAACCGATGAATACAAAGTACCTTCAAAGAAATTTAAGGTGTTGGGGAA
CACAGACCGTCATTCGATTAAAAAGAATCTTATCGGTGCCCTCCTATTCGATAGTGGCGAAACGGCAGAGGCGA
CTCGCCTGAAACGAACCGCTCGGAGAAGGTATACACGTCGCAAGAACCGAATATGTTACTTACAAGAAATTTT
AGCAATGAGATGGCCAAAGTTGACGATTCTTTCTTTCACCGTTTGGAAGAGTCCTTCCTTGTCGAAGAGGACAA
GAAACATGAACGGCACCCCATCTTTGGAAACATAGTAGATGAGGTGGCATATCATGAAAAGTACCCAACGATTT
ATCACCTCAGAAAAAGCTAGTTGACTCAACTGATAAAGCGGACCTGAGGTTAATCTACTTGGCTCTTGCCCAT
ATGATAAAGTTCCGTGGGCACTTTCTCATTGAGGGTGATCTAAATCCGGACAACTCGGATGTCGACAAACTGTT
CATCCAGTTAGTACAAACCTATAATCAGTTGTTTGAAGAGAACCCTATAAATGCAAGTGGCGTGGATGCGAAG
GCTATTCTTAGCGCCCGCCTCTCTAAATCCCGACGGCTAGAAAACCTGATCGCACAATTACCCGGAGAGAAGAA
AAATGGGTTGTTCGGTAACCTTATAGCGCTCTCACTAGGCCTGACACCAAATTTTAAGTCGAACTTCGACTTAGC
TGAAGATGCCAAATTGCAGCTTAGTAAGGACACGTACGATGACGATCTCGACAATCTACTGGCACAAATTGGA
GATCAGTATGCGGACTTATTTTTGGCTGCCAAAAACCTTAGCGATGCAATCCTCCTATCTGACATACTGAGAGTT
AATACTGAGATTACCAAGGCGCCGTTATCCGCTTCAATGATCAAAAGGTACGATGAACATCACCAAGACTTGAC
ACTTCTCAAGGCCCTAGTCCGTCAGCAACTGCCTGAGAAATATAAGGAAATATTCTTTGATCAGTCGAAAAACG
GGTACGCAGGTTATATTGACGGCGGAGCGAGTCAAGAGGAATTCTACAAGTTTATCAAACCCATATTAGAGAA
GATGGATGGGACGGAAGAGTTGCTTGTAAAACTCAATCGCGAAGATCTACTGCGAAAGCAGCGGACTTTCGAC
AACGGTAGCATTCCACATCAAATCCACTTAGGCGAATTGCATGCTATACTTAGAAGGCAGGAGGATTTTTATCC
GTTCCTCAAAGACAATCGTGAAAAGATTGAGAAAATCCTAACCTTTCGCATACCTTACTATGTGGGACCCCTGG
CCCGAGGGAACTCTCGGTTCGCATGGATGACAAGAAAGTCCGAAGAAACGATTACTCCATGGAATTTTGAGGA
AGTTGTCGATAAAGGTGCGTCAGCTCAATCGTTCATCGAGAGGATGACCAACTTTGACAAGAATTTACCGAACG
AAAAAGTATTGCCTAAGCACAGTTTACTTTACGAGTATTTCACAGTGTACAATGAACTCACGAAAGTTAAGTAT
GTCACTGAGGGCATGCGTAAACCCGCCTTTCTAAGCGGAGAACAGAAGAAAGCAATAGTAGATCTGTTATTCA
AGACCAACCGCAAAGTGACAGTTAAGCAATTGAAAGAGGACTACTTTAAGAAAATTGAATGCTTCGATTCTGTC
GAGATCTCCGGGGTAGAAGATCGATTTAATGCGTCACTTGGTACGTATCATGACCTCCTAAAGATAATTAAAGA
TAAGGACTTCCTGGATAACGAAGAGAATGAAGATATCTTAGAAGATATAGTGTTGACTCTTACCCTCTTTGAAG
ATCGGGAAATGATTGAGGAAAGACTAAAAACATACGCTCACCTGTTCGACGATAAGGTTATGAAACAGTTAAA
GAGGCGTCGCTATACGGGCTGGGACGATTGTCGCGGAAACTTATCAACGGGATAAGAGACAAGCAAAGTGG
TAAAACTATTCTCGATTTTCTAAAGAGCGACGGCTTCGCCAATAGGAACTTTATGCAGCTGATCCATGATGACTC
TTTAACCTTCAAAGAGGATATACAAAAGGCACAGGTTTCCGGACAAGGGGACTCATTGCACGAACATATTGCG
AATCTTGCTGGTTCGCCAGCCATCAAAAAGGGCATACTCCAGACAGTCAAAGTAGTGGATGAGCTAGTTAAGG
TCATGGGACGTCACAAACCGGAAAACATTGTAATCGAGATGGCACGCGAAAATCAAACGACTCAGAAGGGGC
AAAAAAACAGTCGAGAGCGGATGAAGAGAATAGAAGAGGGTATTAAAGAACTGGGCAGCCAGATCTTAAAG
GAGCATCCTGTGGAAAATACCCAATTGCAGAACGAGAAACTTTACCTCTATTACCTACAAAATGGAAGGGACAT
GTATGTTGATCAGGAACTGGACATAAACCGTTTATCTGATTACGACGTCGATgcCATTGTACCCCAATCCTTTTG
AAGGACGATTCAATCGACAATAAAGTGCTTACACGCTCGGATAAGAACCGAGGGAAAAGTGACAATGTTCCAA
GCGAGGAAGTCGTAAAGAAAATGAAGAACTATTGGCGGCAGCTCCTAAATGCGAAACTGATAACGCAAAGAA
AGTTCGATAACTTAACTAAAGCTGAGAGGGGTGGCTTGTCTGAACTTGACAAGGCCGGATTTATTAAACGTCAG
CTCGTGGAAACCCGCCAAATCACAAAGCATGTTGCACAGATACTAGATTCCCGAATGAATACGAAATACGACGA
```

FIG. 6 (Continued) - MV-T7-Cas9 recoded D10A/H840A-3XFLAG-VP64

```
GAACGATAAGCTGATTCGGGAAGTCAAAGTAATCACTTTAAAGTCAAAATTGGTGTCGGACTTCAGAAAGGAT
TTTCAATTCTATAAAGTTAGGGAGATAAATAACTACCACCATGCGCACGACGCTTATCTTAATGCCGTCGTAGG
GACCGCACTCATTAAGAAATACCCGAAGCTAGAAAGTGAGTTTGTGTATGGTGATTACAAAGTTTATGACGTCC
GTAAGATGATCGCGAAAAGCGAACAGGAGATAGGCAAGGCTACAGCCAAATACTTCTTTTATTCTAACATTATG
AATTTCTTTAAGACGGAAATCACTCTGGCAAACGGAGAGATACGCAAACGACCTTTAATTGAAACCAATGGGG
AGACAGGTGAAATCGTATGGGATAAGGGCCGGGACTTCGCGACGGTGAGAAAAGTTTTGTCCATGCCCCAAGT
CAACATAGTAAAGAAAACTGAGGTGCAGACCGGAGGGTTTTCAAAGGAATCGATTCTTCCAAAAAGGAATAGT
GATAAGCTCATCGCTCGTAAAAAGGACTGGGACCCGAAAAAGTACGGTGGCTTCGATAGCCCTACAGTTGCCT
ATTCTGTCCTAGTAGTGGCAAAAGTTGAGAAGGGAAAATCCAAGAAACTGAAGTCAGTCAAAGAATTATTGGG
GATAACGATTATGGAGCGCTCGTCTTTTGAAAAGAACCCCATCGACTTCCTTGAGGCGAAAGGTTACAAGGAA
GTAAAAAAGGATCTCATAATTAAACTACCAAAGTATAGTCTGTTTGAGTTAGAAAATGGCCGAAAACGGATGTT
GGCTAGCGCCGGAGAGCTTCAAAAGGGGAACGAACTCGCACTACCGTCTAAATACGTGAATTTCCTGTATTTAG
CGTCCCATTACGAGAAGTTGAAAGGTTCACCTGAAGATAACGAACAGAAGCAACTTTTTGTTGAGCAGCACAAA
CATTATCTCGACGAAATCATAGAGCAAATTTCGGAATTCAGTAAGAGAGTCATCCTAGCTGATGCCAATCTGGA
CAAAGTATTAAGCGCATACAACAAGCACAGGGATAAACCCATACGTGAGCAGGCGGAAAATATTATCCATTTG
TTTACTCTTACCAACCTCGGCGCTCCAGCCGCATTCAAGTATTTTGACACAACGATAGATCGCAAACGATACACT
TCTACCAAGGAGGTGCTAGACGCGACACTGATTCACCAATCCATCACGGGATTATATGAAACTCGGATAGATTT
GTCACAGCTTGGGGGTGACGGATCCCCCAAGAAGAAGAGGAAAGTCTCGAGCGACTACAAAGACCATGACGG
TGATTATAAAGATCATGACATCGATTACAAGGATGACGATGACAAGGctgcaggaggcggtggaagcGGGCGCGCCG
ACGCGCTGGACGATTTCGATCTCGACATGCTGGGTTCTGATGCCCTCGATGACTTTGACCTGGATATGTTGGGA
AGCGACGCATTGGATGACTTTGATCTGGACATGCTCGGCTCCGATGCTCTGGACGATTTCGATCTCGATATGTT
ATAAccggtCATCATCACCATCACCATTGAGTTTAAACCCGCTGATCAGCCTCGACTGTGCCTTCTAGTTGCCAGC
CATCTGTTGTTTGCCCCTCCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGTGGGGCAGGACAGCAA
GGGGGAGGATTGGGAAGACAATAGCAGGCATGCTGGGGATGCGGTGGGCTCTATGGCTTCTGAGGCGGAAA
GAACCAGCTGGGGCTCGATACCGTCGACCTCTAGCTAGAGCTTGGCGTAATCATGGTCATAGCTGTTTCCTGTG
TGAAATTGTTATCCGCTCACAATTCCACACAACATACGAGCCGGAAGCATAAAGTGTAAAGCCTAGGGTGCCTA
ATGAGTGAGCTAACTCACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTGGGCGCTCTTCCGCTTCCTCGCTCACTG
ACTCGCTGCGCTCGGTCGTTCGGCTGCGGCGAGCGGTATCAGCTCACTCAAAGGCGGTAATACGGTTATCCACA
GAATCAGGGGATAACGCAGGAAAGAACATGTGAGCAAAAGGCCAGCAAAAGGCCAGGAACCGTAAAAAGGC
CGCGTTGCTGGCGTTTTTCCATAGGCTCCGCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGCGCTTTCTCAATGCTCACGCTGT
AGGTATCTCAGTTCGGTGTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAGTGGTGGCCTAACTACGG
CTACACTAGAAGGACAGTATTTGGTATCTGCGCTCTGCTGAAGCCAGTTACCTTCGGAAAAAGAGTTGGTAGCT
CTTGATCCGGCAAACAAACCACCGCTGGTAGCGGTGGTTTTTTGTTTGCAAGCAGCAGATTACGCGCAGAAAA
AAAGGATCTCAAGAAGATCCTTTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGGCTTACCATCTGG
CCCCAGTGCTGCAATGATACCGCGAGACCCACGCTCACCGGCTCCAGATTTATCAGCAATAAACCAGCCAGCCG
GAAGGGCCGAGCGCAGAAGTGGTCCTGCAACTTTATCCGCCTCCATCCAGTCTATTAATTGTTGCCGGGAAGCT
AGAGTAAGTAGTTCGCCAGTTAATAGTTTGCGCAACGTTGTTGCCATTGCTACAGGCATCGTGGTGTCACGCTC
```

| FIG. 6 (Continued) - MV-T7-Cas9 recoded D10A/H840A-3XFLAG-VP64 |
| --- |
| GTCGTTTGGTATGGCTTCATTCAGCTCCGGTTCCCAACGATCAAGGCGAGTTACATGATCCCCCATGTTGTGCAA |
| AAAAGCGGTTAGCTCCTTCGGTCCTCCGATCGTTGTCAGAAGTAAGTTGGCCGCAGTGTTATCACTCATGGTTAT |
| GGCAGCACTGCATAATTCTCTTACTGTCATGCCATCCGTAAGATGCTTTTCTGTGACTGGTGAGTACTCAACCAA |
| GTCATTCTGAGAATAGTGTATGCGGCGACCGAGTTGCTCTTGCCCGGCGTCAATACGGGATAATACCGCGCCAC |
| ATAGCAGAACTTTAAAAGTGCTCATCATTGGAAAACGTTCTTCGGGGCGAAAACTCTCAAGGATCTTACCGCTG |
| TTGAGATCCAGTTCGATGTAACCCACTCGTGCACCCAACTGATCTTCAGCATCTTTTACTTTCACCAGCGTTTCTG |
| GGTGAGCAAAAACAGGAAGGCAAAATGCCGCAAAAAAGGGAATAAGGGCGACACGGAAATGTTGAATACTC |
| ATACTCTTCCTTTTTCAATATTATTGAAGCATTTATCAGGGTTATTGTCTCATGAGCGGATACATATTTGAATGTA |
| TTTAGAAAAATAAACAAATAGGGGTTCCGCGCACATTTCCCCGAAAAGTGCCACCTGACGTCGACGGATCGGG |
| AGATCGATCTCCCGATCCCCTAGGGTCGACTCTCAGTACAATCTGCTCTGATGCCGCATAGTTAAGCCAGTATCT |
| GCTCCCTGCTTGTGTGTTGGAGGTCGCTGAGTAGTGCGCGAGCAAAATTTAAGCTACAACAAGGCAAGGCTTG |
| ACCGACAATTGCATGAAGAATCTGCTTAGGGTTAGGCGTTTTGCGCTGCTTCGCGATGTACGGGCCAGATATAC |
| GCGTTGACATTGATTATTGACTAGTTATTAATAGTAATCAATTACGGGGTCATTAGTTCATAGCCCATATATGGA |
| GTTCCGCGTTACATAACTTACGGTAAATGGCCCGCCTGGCTGACCGCCCAACGACCCCCGCCCATTGACGTCAA |
| TAATGACGTATGTTCCCATAGTAACGCCAATAGGGACTTTCCATTGACGTCAATGGGTGGACTATTTACGGTAA |
| ACTGCCCACTTGGCAGTACATCAAGTGTATC (SEQ ID NO:6) |

FIG. 7 - Cas9-activator protein

MDKKYSIGLAIGTNSVGWAVITDEYKVPSKKFKVLGNTDRHSIKKNLIGALLFDS
GETAEATRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARLSKSRRLE
NLIAQLPGEKKNGLFGNLIALSLGLTPNFKSNFDLAEDAKLQLSKDTYDDDLDNLL
AQIGDQYADLFLAAKNLSDAILLSDILRVNTEITKAPLSASMIKRYDEHHQDLTLLK
ALVRQQLPEKYKEIFFDQSKNGYAGYIDGGASQEEFYKFIKPILEKMDGTEELLVK
LNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLP
NEKVLPKHSLLYEYFTVYNELTKVKYVTEGMRKPAFLSGEQKKAIVDLLFKTNRKV
TVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIR
DKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSR
ERMKRIEEGIKELGSQILKEHPVENTQLQNEKLYLYYLQNGRDMYVDQELDINRL
SDYDVDAIVPQSFLKDDSIDNKVLTRSDKNRGKSDNVPSEEVVKKMKNYWRQL
LNAKLITQRKFDNLTKAERGGLSELDKAGFIKRQLVETRQITKHVAQILDSRMNT
KYDENDKLIREVKVITLKSKLVSDFRKDFQFYKVREINNYHHAHDAYLNAVVGTA
LIKKYPKLESEFVYGDYKVYDVRKMIAKSEQEIGKATAKYFFYSNIMNFFKTEITLA
NGEIRKRPLIETNGETGEIVWDKGRDFATVRKVLSMPQVNIVKKTEVQTGGFSK
ESILPKRNSDKLIARKKDWDPKKYGGFDSPTVAYSVLVVAKVEKGKSKKLKSVKEL
LGITIMERSSFEKNPIDFLEAKGYKEVKKDLIIKLPKYSLFELENGRKRMLASAGEL
QKGNELALPSKYVNFLYLASHYEKLKGSPEDNEQKQLFVEQHKHYLDEIIEQISEF
SKRVILADANLDKVLSAYNKHRDKPIREQAENIIHLFTLTNLGAPAAFKYFDTTIDR
KRYTSTKEVLDATLIHQSITGLYETRIDLSQLGGDGSpkkkrkvss<u>DYKDHDGDYKD
HDIDYKDDDDKAA</u>GGGGSGRADALDDFDLDMLGSDALDDFDLDMLGSDAL
DDFDLDMLGSDALDDFDLDML (SEQ ID NO:7)

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: nuclear localization signal

<400> SEQUENCE: 1

Pro Lys Lys Lys Arg Lys Val Ser
1               5

<210> SEQ ID NO 2
<211> LENGTH: 50
<212> TYPE: PRT
<213> ORGANISM: Artificial Sequence
```

```
<220> FEATURE:
<223> OTHER INFORMATION: VP64 transcriptional activator sequence

<400> SEQUENCE: 2

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50

<210> SEQ ID NO 3
<211> LENGTH: 1368
<212> TYPE: PRT
<213> ORGANISM: Artificial Sequence
<220> FEATURE:
<223> OTHER INFORMATION: catalytically inactive Cas9

<400> SEQUENCE: 3

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
```

```
              275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
    690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala Lys
        1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
            1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
        1075                1080                1085

Met Pro Gln Val Asn Ile Val Lys Lys Thr Glu Val Gln Thr Gly Gly
    1090                1095                1100

Phe Ser Lys Glu Ser Ile Leu Pro Lys Arg Asn Ser Asp Lys Leu Ile
1105                1110                1115                1120
```

Ala Arg Lys Lys Asp Trp Asp Pro Lys Lys Tyr Gly Gly Phe Asp Ser
            1125                1130                1135

Pro Thr Val Ala Tyr Ser Val Leu Val Val Ala Lys Val Glu Lys Gly
        1140                1145                1150

Lys Ser Lys Lys Leu Lys Ser Val Lys Glu Leu Leu Gly Ile Thr Ile
        1155                1160                1165

Met Glu Arg Ser Ser Phe Glu Lys Asn Pro Ile Asp Phe Leu Glu Ala
        1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
            1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
            1315                1320                1325

Thr Thr Ile Asp Arg Lys Arg Tyr Thr Ser Thr Lys Glu Val Leu Asp
        1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp
            1365

```
<210> SEQ ID NO 4
<211> LENGTH: 2279
<212> TYPE: DNA
<213> ORGANISM: Artificial Sequence
<220> FEATURE:
<223> OTHER INFORMATION: guide RNA expression vector sequence
<220> FEATURE:
<221> NAME/KEY: misc_feature
<222> LOCATION: (331)...(350)
<223> OTHER INFORMATION: n = A, T, C or G

<400> SEQUENCE: 4
gacgtcgcta gctgtacaaa aaagcaggct ttaaaggaac caattcagtc gactggatcc      60
ggtaccaagg tcgggcagga agagggccta tttcccatga ttccttcata tttgcatata     120
cgatacaagg ctgttagaga gataattaga attaatttga ctgtaaacac aaagatatta     180
gtacaaaata cgtgacgtag aaagtaataa tttcttgggt agtttgcagt tttaaaatta     240
tgttttaaaa tggactatca tatgcttacc gtaacttgaa agtatttcga tttcttggct     300
ttatatatct tgtggaaagg acgaaacacc nnnnnnnnnn nnnnnnnnnn gttttagagc     360
tagaaatagc aagttaaaat aaggctagtc cgttatcaac ttgaaaaagt ggcaccgagt     420
cggtgctttt tttaagcttg gccgctcga ggtacctctc tacatatgac atgtgagcaa     480
aaggccagca aaaggccagg aaccgtaaaa aggccgcgtt gctggcgttt tccataggc     540
```

```
tccgccccce tgacgagcat cacaaaaatc gacgctcaag tcagaggtgg cgaaacccga      600
caggactata aagataccag gcgttteeee etggaagete cetegtgege tetectgtte      660 cgaccctgcc gcttaccgga tacctgtccg cctttctccc ttcgggaagc gtggcgcttt      720
ctcatagctc acgctgtagg tatctcagtt cggtgtaggt cgttcgctcc aagctgggct      780
gtgtgcacga accccccgtt cagcccgacc gctgcgcctt atccggtaac tatcgtcttg      840
agtccaaccc ggtaagacac gacttatcgc cactggcagc agccactggt aacaggatta      900
gcagagcgag gtatgtaggc ggtgctacag agttcttgaa gtggtggcct aactacggct      960
acactagaag aacagtattt ggtatctgcg ctctgctgaa gccagttacc ttcggaaaaa     1020
gagttggtag ctcttgatcc ggcaaacaaa ccaccgctgg tagcggtggt ttttttgttt     1080
gcaagcagca gattacgcgc agaaaaaaag gatctcaaga agatcctttg atcttttcta     1140
cggggtctga cgctcagtgg aacgaaaact cacgttaagg gattttggtc atgagattat     1200
caaaaaggat cttcacctag atccttttaa attaaaaatg aagttttaaa tcaatctaaa     1260
gtatatatga gtaaacttgg tctgacagtt accaatgctt aatcagtgag gcacctatct     1320
cagcgatctg tctatttcgt tcatccatag ttgcctgact ccccgtcgtg tagataacta     1380
cgatacggga gggcttacca tctggcccca gtgctgcaat gataccgcga gacccacgct     1440
caccggctcc agatttatca gcaataaacc agccagccgg aagggccgag cgcagaagtg     1500
gtcctgcaac tttatccgcc tccatccagt ctattaattg ttgccgggaa gctagagtaa     1560
gtagttcgcc agttaatagt ttgcgcaacg ttgttgccat tgctacaggc atcgtggtgt     1620
cacgctcgtc gtttggtatg gcttcattca gctccggttc ccaacgatca aggcgagtta     1680
catgatcccc catgttgtgc aaaaaagcgg ttagctcctt cggtcctccg atcgttgtca     1740
gaagtaagtt ggccgcagtg ttatcactca tggttatggc agcactgcat aattctctta     1800
ctgtcatgcc atccgtaaga tgcttttctg tgactggtga gtactcaacc aagtcattct     1860
gagaatagtg tatgcggcga ccgagttgct cttgcccggc gtcaatacgg gataataccg     1920
cgccacatag cagaacttta aaagtgctca tcattggaaa acgttcttcg ggcgaaaac      1980 tctcaaggat cttaccgctg ttgagatcca gttcgatgta acccactcgt gcacccaact     2040
gatcttcagc atcttttact ttcaccagcg tttctgggtg agcaaaaaca ggaaggcaaa     2100
atgccgcaaa aaagggaata agggcgacac ggaaatgttg aatactcata ctcttccttt     2160
ttcaatatta ttgaagcatt tatcagggtt attgtctcat gagcggatac atatttgaat     2220
gtatttagaa aaataaacaa atagggttc cgcgcacatt tccccgaaaa gtgccacct      2279
```

<210> SEQ ID NO 5
<211> LENGTH: 7786
<212> TYPE: DNA
<213> ORGANISM: Artificial Sequence
<220> FEATURE:
<223> OTHER INFORMATION: CMV-T7-Cas9 D10A/H840A-3xFLAG-VP64 sequence

<400> SEQUENCE: 5

```
atatgccaag tacgccccct attgacgtca atgacggtaa atggcccgcc tggcattatg       60
cccagtacat gaccttatgg gactttccta cttggcagta catctacgta ttagtcatcg      120
ctattaccat ggtgatgcgg ttttggcagt acatcaatgg gcgtggatag cggtttgact      180
cacggggatt tccaagtctc cacccccattg acgtcaatgg gagtttgttt tggcaccaaa     240
atcaacggga ctttccaaaa tgtcgtaaca actccgcccc attgacgcaa atgggcggta      300
```

```
ggcgtgtacg gtgggaggtc tatataagca gagctggttt agtgaaccgt cagatccgct      360
agagatccgc ggccgctaat acgactcact ataggagag ccgccaccat ggataagaaa        420
tactcaatag gcttagctat cggcacaaat agcgtcggat gggcggtgat cactgatgaa       480
tataaggttc cgtctaaaaa gttcaaggtt ctgggaaata cagaccgcca cagtatcaaa       540
aaaaatctta tagggctct tttatttgac agtggagaga cagcggaagc gactcgtctc        600
aaacggacag ctcgtagaag gtatacacgt cggaagaatc gtatttgtta tctacaggag       660 atttttcaa atgagatggc gaaagtagat gatagtttct tcatcgact tgaagagtct         720 tttttggtgg aagaagacaa gaagcatgaa cgtcatccta tttttggaaa tatagtagat       780
gaagttgctt atcatgagaa atatccaact atctatcatc tgcgaaaaaa attggtagat       840
tctactgata aagcggattt gcgcttaatc tatttggcct tagcgcatat gattaagttt       900
cgtggtcatt ttttgattga gggagattta atcctgata atagtgatgt ggacaaacta        960
tttatccagt tggtacaaac ctacaatcaa ttatttgaag aaaacccta taacgcaagt       1020 ggagtagatg ctaaagcgat tctttctgca cgattgagta atcaagacg attagaaaat       1080 ctcattgctc agctccccgg tgagaagaaa aatggcttat ttgggaatct cattgctttg      1140
tcattgggtt tgaccccta ttttaaatca attttgatt tggcagaaga tgctaaatta       1200 cagcttttcaa aagatactta cgatgatgat ttagataatt tattggcgca aattggagat     1260
caatatgctg atttgttttt ggcagctaag aatttatcag atgctatttt actttcagat      1320
atcctaagag taaatactga aataactaag gctcccctat cagcttcaat gattaaacgc      1380
tacgatgaac atcatcaaga cttgactctt ttaaaagctt tagttcgaca acaacttcca     1440
gaaaagtata agaaatcttt ttttgatcaa tcaaaaaacg gatatgcagg ttatattgat      1500
gggggagcta gccaagaaga atttttataaa tttatcaaac caattttaga aaaaatggat    1560
ggtactgagg aattattggt gaaactaaat cgtgaagatt tgctgcgcaa gcaacggacc      1620
tttgacaacg gctctattcc ccatcaaatt cacttgggtg agctgcatgc tatttttgaga    1680 agacaagaag actttttatcc attttttaaa gacaatcgtg agaagattga aaaaatcttg    1740
acttttcgaa ttccttatta tgttggtcca ttggcgcgtg gcaatagtcg ttttgcatgg     1800
atgactcgga agtctgaaga aacaattacc ccatggaatt ttgaagaagt tgtcgataaa     1860
ggtgcttcag ctcaatcatt tattgaacgc atgacaaact tgataaaaaa tcttccaaat     1920
gaaaaagtac taccaaaaca tagtttgctt tatgagtatt ttacggttta taacgaattg     1980
acaaaggtca aatatgttac tgaaggaatg cgaaaaccag catttctttc aggtgaacag     2040
aagaaagcca ttgttgattt actcttcaaa acaaatcgaa agtaaccgt taagcaatta     2100 aaagaagatt atttcaaaaa aatagaatgt tttgatagtg ttgaaatttc aggagttgaa     2160
gatagattta atgcttcatt aggtacctac catgatttgc taaaaattat taagataaa      2220 gattttttgg ataatgaaga aaatgaagat atcttagagg atattgtttt aacattgacc      2280
ttatttgaag atagggagat gattgaggaa agacttaaaa catatgctca cctctttgat     2340
gataaggtga tgaaacagct taacgtcgc cgttatactg gttggggacg tttgtctcga      2400
aaattgatta atggtattag ggataagcaa tctggcaaaa caatattaga ttttttgaaa    2460
tcagatggtt ttgccaatcg caattttatg cagctgatcc atgatgatag tttgacattt     2520 aagaagaca ttcaaaaagc acaagtgtct ggacaaggcg atagttacca tgaacatatt     2580
gcaaatttag ctggtagccc tgctattaaa aaaggtattt tacagactgt aaaagttgtt    2640
gatgaattgg tcaaagtaat ggggcggcat aagccagaaa atatcgttat tgaaatggca     2700
```

```
cgtgaaaatc agacaactca aaagggccag aaaaattcgc gagagcgtat gaaacgaatc    2760
gaagaaggta tcaaagaatt aggaagtcag attcttaaag agcatcctgt tgaaaatact    2820
caattgcaaa atgaaaagct ctatctctat tatctccaaa atggaagaga catgtatgtg    2880
gaccaagaat tagatattaa tcgtttaagt gattatgatg tcgatgccat tgttccacaa    2940
agtttcctta aagacgattc aatagacaat aaggtcttaa cgcgttctga taaaaatcgt    3000
ggtaaatcgg ataacgttcc aagtgaagaa gtagtcaaaa agatgaaaaa ctattggaga    3060
caacttctaa acgccaagtt aatcactcaa cgtaagtttg ataatttaac gaaagctgaa    3120
cgtggaggtt tgagtgaact tgataaagct ggttttatca aacgccaatt ggttgaaact    3180
cgccaaatca ctaagcatgt ggcacaaatt ttggatagtc gcatgaatac taaatacgat    3240
gaaaatgata aacttattcg agaggttaaa gtgattacct aaaatctaaa attagtttct    3300
gacttccgaa aagatttcca attctataaa gtacgtgaga ttaacaatta ccatcatgcc    3360
catgatgcgt atctaaatgc cgtcgttgga actgctttga ttaagaaata tccaaaactt    3420
gaatcggagt ttgtctatgg tgattataaa gtttatgatg ttcgtaaaat gattgctaag    3480
tctgagcaag aaataggcaa agcaaccgca aaatatttct tttactctaa tatcatgaac    3540
ttcttcaaaa cagaaattac acttgcaaat ggagagattc gcaaacgccc tctaatcgaa    3600
actaatgggg aaactggaga aattgtctgg gataaagggc gagattttgc cacagtgcgc    3660
aaagtattgt ccatgcccca agtcaatatt gtcaagaaaa cagaagtaca gacaggcgga    3720
ttctccaagg agtcaatttt accaaaaaga aattcggaca agcttattgc tcgtaaaaaa    3780
gactgggatc aaaaaaata tggtggtttt gatagtccaa cggtagctta ttcagtccta    3840
gtggttgcta aggtggaaaa agggaaatcg aagaagttaa aatccgttaa agagttacta    3900
gggatcacaa ttatggaaag aagttccttt gaaaaaaatc cgattgactt tttagaagct    3960
aaaggatata aggaagttaa aaaagactta atcattaaac tacctaaata tagtcttttt    4020
gagttagaaa acggtcgtaa acggatgctg gctagtgccg gagaattaca aaaaggaaat    4080
gagctggctc tgccaagcaa atatgtgaat ttttatatt tagctagtca ttatgaaaag    4140
ttgaagggta gtccagaaga taacgaacaa aaacaattgt tgtggagca gcataagcat    4200 tatttagatg agattattga gcaaatcagt gaattttcta agcgtgttat tttagcagat    4260
gccaatttag ataaagttct tagtgcatat aacaaacata gagacaaacc aatacgtgaa    4320
caagcagaaa atattattca tttatttacg ttgacgaatc ttggagctcc cgctgctttt    4380
aaatattttg atacaacaat tgatcgtaaa cgatatacgt ctacaaaaga gttttagat     4440 gccactctta tccatcaatc catcactggt ctttatgaaa cacgcattga tttgagtcag    4500
ctaggaggtg acggttctcc caagaagaag aggaaagtct cgagcgacta caaagaccat    4560
gacggtgatt ataaagatca tgacatcgat tacaaggatg acgatgacaa ggctgcagga    4620
ggcggtggaa gcgggcgcgc cgacgcgctg gacgatttcg atctcgacat gctgggttct    4680
gatgccctcg atgactttga cctggatatg ttgggaagcg acgcattgga tgactttgat    4740
ctggacatgc tcggctccga tgctctggac gatttcgatc tcgatatgtt ataaccggtc    4800
atcatcacca tcaccattga gtttaaaccc gctgatcagc ctcgactgtg ccttctagtt    4860
gccagccatc tgttgtttgc ccctcccccg tgccttcctt gaccctggaa ggtgccactc    4920
ccactgtcct ttcctaataa aatgaggaaa ttgcatcgca ttgtctgagt aggtgtcatt    4980
ctattctggg gggtggggtg gggcaggaca gcaagggggga ggattgggaa gacaatagca    5040
```

```
ggcatgctgg ggatgcggtg ggctctatgg cttctgaggc ggaaagaacc agctggggct      5100
cgataccgtc gacctctagc tagagcttgg cgtaatcatg gtcatagctg tttcctgtgt      5160
gaaattgtta tccgctcaca attccacaca acatacgagc cggaagcata agtgtaaag       5220 cctagggtgc ctaatgagtg agctaactca cattaattgc gttgcgctca ctgcccgctt      5280
tccagtcggg aaacctgtcg tgccagctgc attaatgaat cggccaacgc gcggggagag      5340
gcggtttgcg tattgggcgc tcttccgctt cctcgctcac tgactcgctg cgctcggtcg      5400
ttcggctgcg gcgagcggta tcagctcact caaaggcggt aatacggtta ccacagaat      5460 caggggataa cgcaggaaag aacatgtgag caaaaggcca gcaaaaggcc aggaaccgta      5520
aaaaggccgc gttgctggcg ttttttccata ggctccgccc ccctgacgag catcacaaaa     5580
atcgacgctc aagtcagagg tggcgaaacc cgacaggact ataaagatac caggcgtttc     5640
cccctggaag ctccctcgtg cgctctcctg ttccgaccct gccgcttacc ggatacctgt     5700
ccgcctttct cccttcggga agcgtggcgc tttctcaatg ctcacgctgt aggtatctca     5760
gttcggtgta ggtcgttcgc tccaagctgg gctgtgtgca cgaaccccc gttcagcccg      5820 accgctgcgc cttatccggt aactatcgtc ttgagtccaa cccggtaaga cacgacttat     5880
cgccactggc agcagccact ggtaacagga ttagcagagc gaggtatgta ggcggtgcta     5940
cagagttctt gaagtggtgg cctaactacg gctacactag aaggacagta tttggtatct     6000
gcgctctgct gaagccagtt accttcggaa aaagagttgg tagctcttga tccggcaaac     6060
aaaccaccgc tggtagcggt ggtttttttg tttgcaagca gcagattacg cgcagaaaaa     6120
aaggatctca agaagatcct ttgatctttt ctacggggtc tgacgctcag tggaacgaaa     6180
actcacgtta agggattttg gtcatgagat tatcaaaaag gatcttcacc tagatccttt     6240
taaattaaaa atgaagtttt aaatcaatct aaagtatata tgagtaaact tggtctgaca     6300
gttaccaatg cttaatcagt gaggcaccta tctcagcgat ctgtctattt cgttcatcca     6360
tagttgcctg actccccgtc gtgtagataa ctacgatacg ggagggctta ccatctggcc     6420
ccagtgctgc aatgataccg cgagacccac gctcaccggc tccagattta tcagcaataa     6480
accagccagc cggaagggcc gagcgcagaa gtggtcctgc aactttatcc gcctccatcc     6540
agtctattaa ttgttgccgg gaagctagag taagtagttc gccagttaat agtttgcgca     6600
acgttgttgc cattgctaca ggcatcgtgg tgtcacgctc gtcgtttggt atggcttcat     6660
tcagctccgg ttcccaacga tcaaggcgag ttacatgatc ccccatgttg tgcaaaaaag     6720
cggttagctc cttcggtcct ccgatcgttg tcagaagtaa gttggccgca gtgttatcac     6780
tcatggttat ggcagcactg cataattctc ttactgtcat gccatccgta agatgctttt     6840
ctgtgactgg tgagtactca accaagtcat tctgagaata gtgtatgcgg cgaccgagtt     6900
gctcttgccc ggcgtcaata cgggataata ccgcgccaca tagcagaact ttaaaagtgc     6960
tcatcattgg aaaacgttct cggggcgaa aactctcaag gatcttaccg ctgttgagat      7020
ccagttcgat gtaacccact cgtgcaccca actgatcttc agcatctttt actttcacca     7080
gcgtttctgg gtgagcaaaa acaggaaggc aaaatgccgc aaaaaaggga ataagggcga     7140
cacggaaatg ttgaatactc atactcttcc tttttcaata ttattgaagc atttatcagg     7200
gttattgtct catgagcgga tacatatttg aatgtattta gaaaaataaa caaataggg     7260 ttccgcgcac atttccccga aaagtgccac ctgacgtcga cggatcggga gatcgatctc     7320
ccgatcccct agggtcgact ctcagtacaa tctgctctga tgccgcatag ttaagccagt     7380
atctgctccc tgcttgtgtg ttggaggtcg ctgagtagtg cgcgagcaaa atttaagcta     7440
```

-continued

```
caacaaggca aggcttgacc gacaattgca tgaagaatct gcttagggtt aggcgttttg      7500
cgctgcttcg cgatgtacgg gccagatata cgcgttgaca ttgattattg actagttatt      7560
aatagtaatc aattacgggg tcattagttc atagcccata tatggagttc cgcgttacat      7620
aacttacggt aaatggcccg cctggctgac cgcccaacga ccccgccca ttgacgtcaa       7680 taatgacgta tgttcccata gtaacgccaa tagggacttt ccattgacgt caatgggtgg      7740
actatttacg gtaaactgcc cacttggcag tacatcaagt gtatcc                     7786
```

<210> SEQ ID NO 6
<211> LENGTH: 7785
<212> TYPE: DNA
<213> ORGANISM: Artificial Sequence
<220> FEATURE:
<223> OTHER INFORMATION: MV-T7-Cas9 recoded D10A/H840A-3xFLAG-VP64
      sequence

<400> SEQUENCE: 6

```
atatgccaag tacgccccct attgacgtca atgacggtaa atggcccgcc tggcattatg        60
cccagtacat gaccttatgg gactttccta cttggcagta catctacgta ttagtcatcg       120
ctattaccat ggtgatgcgg ttttggcagt acatcaatgg gcgtggatag cggtttgact       180
cacggggatt tccaagtctc cacccattg acgtcaatgg gagtttgttt tggcaccaaa       240
atcaacggga ctttccaaaa tgtcgtaaca actccgcccc attgacgcaa atgggcggta       300
ggcgtgtacg gtgggaggtc tatataagca gagctggttt agtgaaccgt cagatccgct       360
agagatccgc ggccgctaat acgactcact atagggagag ccgccaccat ggataaaaag       420
tattctattg gtttagccat cggcactaat tccgttggat gggctgtcat aaccgatgaa       480
tacaaagtac cttcaaagaa atttaaggtg ttggggaaca cagaccgtca ttcgattaaa       540
aagaatctta tcggtgccct cctattcgat agtggcgaaa cggcagaggc gactcgcctg       600
aaacgaaccg ctcggagaag gtatacacgt cgcaagaacc gaatatgtta cttacaagaa       660
atttttagca atgagatggc caaagttgac gattctttct tcaccgtttt ggaagagtcc       720
ttccttgtcg aagaggacaa gaaacatgaa cggcacccca tctttggaaa catagtagat       780
gaggtggcat atcatgaaaa gtacccaacg atttatcacc tcagaaaaaa gctagttgac       840
tcaactgata agcggaccct gaggttaatc tacttggctc ttgcccatat gataaagttc       900
cgtgggcact ttctcattga gggtgatcta aatccggaca actcggatgt cgacaaactg       960
ttcatccagt tagtacaaac ctataatcag ttgtttgaag agaacccat aaaatgcaagt      1020 ggcgtggatg cgaaggctat tcttagcgcc cgcctctcta aatcccgacg gctagaaaac      1080
ctgatcgcac aattacccgg agagaagaaa atgggttgt tcggtaacct tatagcgctc       1140
tcactaggcc tgacaccaaa ttttaagtcg aacttcgact tagctgaaga tgccaaattg      1200
cagcttagta aggacacgta cgatgacgat ctcgacaatc tactggcaca aattggagat       1260
cagtatgcgg acttattttt ggctgccaaa aaccttagcg atgcaatcct cctatctgac       1320
atactgagag ttaatactga gattaccaag gcgccgttat ccgcttcaat gatcaaaagg       1380
tacgatgaac atcaccaaga cttgacactt ctcaaggccc tagtccgtca gcaactgcct       1440
gagaaatata aggaaatatt ctttgatcag tcgaaaaacg ggtacgcagg ttatattgac       1500
ggcggagcga gtcaagagga attctacaag tttatcaaac ccatattaga aaagatggat       1560 gggacgaag agttgcttgt aaaactcaat cgcgaagatc tactgcgaaa gcagcggact       1620
ttcgacaacg gtagcattcc acatcaaatc cacttaggcg aattgcatgc tatacttaga      1680
```

```
aggcaggagg attttttatcc gttcctcaaa gacaatcgtg aaaagattga gaaaatccta    1740
acctttcgca taccttacta tgtgggaccc ctggcccgag ggaactctcg gttcgcatgg    1800
atgacaagaa agtccgaaga aacgattact ccatggaatt ttgaggaagt tgtcgataaa    1860
ggtgcgtcag ctcaatcgtt catcgagagg atgaccaact ttgacaagaa tttaccgaac    1920
gaaaaagtat tgcctaagca cagtttactt tacgagtatt tcacagtgta caatgaactc    1980
acgaaagtta agtatgtcac tgagggcatg cgtaaacccg cctttctaag cggagaacag    2040
aagaaagcaa tagtagatct gttattcaag accaaccgca aagtgacagt taagcaattg    2100
aaagaggact actttaagaa aattgaatgc ttcgattctg tcgagatctc cggggtagaa    2160
gatcgattta atgcgtcact tggtacgtat catgacctcc taaagataat taaagataag    2220
gacttcctgg ataacgaaga gaatgaagat atcttagaag atatagtgtt gactcttacc    2280
ctctttgaag atcgggaaat gattgaggaa agactaaaaa catacgctca cctgttcgac    2340
gataaggtta tgaaacagtt aaagaggcgt cgctatacgg gctggggacg attgtcgcgg    2400
aaacttatca acgggataag agacaagcaa agtggtaaaa ctattctcga ttttctaaag    2460
agcgacggct tcgccaatag gaactttatg cagctgatcc atgatgactc tttaaccttc    2520
aaagaggata tacaaaaggc acaggtttcc ggacaagggg actcattgca cgaacatatt    2580
gcgaatcttg ctggttcgcc agccatcaaa aagggcatac tccagacagt caaagtagtg    2640
gatgagctag ttaaggtcat gggacgtcac aaaccggaaa acattgtaat cgagatggca    2700
cgcgaaaatc aaacgactca gaaggggcaa aaaacagtc gagagcggat gaagagaata    2760
gaagagggta ttaaagaact gggcagccag atcttaaagg agcatcctgt ggaaaatacc    2820
caattgcaga acgagaaact ttacctctat tacctacaaa atggaaggga catgtatgtt    2880
gatcaggaac tggacataaa ccgtttatct gattacgacg tcgatgccat tgtaccccaa    2940
tcctttttga aggacgattc aatcgacaat aaagtgctta cacgctcgga taagaaccga    3000
gggaaaagtg acaatgttcc aagcgaggaa gtcgtaaaga aaatgaagaa ctattggcgg    3060
cagctcctaa atgcgaaact gataacgcaa agaaagttcg ataacttaac taaagctgag    3120 agggggtggct tgtctgaact tgacaaggcc ggatttatta acgtcagct cgtggaaacc    3180 cgccaaatca caagcatgt tgcacagata ctagattccc gaatgaatac gaaatacgac    3240
gagaacgata agctgattcg ggaagtcaaa gtaatcactt taaagtcaaa attggtgtcg    3300
gacttcagaa aggattttca attctataaa gttagggaga taaataacta ccaccatgcg    3360
cacgacgctt atcttaatgc cgtcgtaggg accgcactca ttaagaaata cccgaagcta    3420
gaaagtgagt ttgtgtatgg tgattacaaa gtttatgacg tccgtaagat gatcgcgaaa    3480
agcgaacagg agataggcaa ggctacagcc aaatacttct tttattctaa cattatgaat    3540
ttctttaaga cggaaatcac tctggcaaac ggagagatac gcaaacgacc tttaattgaa    3600
accaatgggg agacaggtga atcgtatggg gataagggcc gggacttcgc gacggtgaga    3660 aaagtttttgt ccatgcccca agtcaacata gtaaagaaaa ctgaggtgca gaccggaggg    3720
ttttcaaagg aatcgattct tccaaaaagg aatagtgata agctcatcgc tcgtaaaaag    3780
gactgggacc cgaaaaagta cggtggcttc gatagcccta cagttgccta ttctgtccta    3840
gtagtggcaa aagttgagaa gggaaaatcc aagaaactga agtcagtcaa agaattattg    3900
gggataacga ttatggagcg ctcgtctttt gaaagaaacc ccatcgactt ccttgaggcg    3960
aaaggttaca aggaagtaaa aaaggatctc ataattaaac taccaaagta tagtctgttt    4020
```

-continued

```
gagttagaaa atggccgaaa acggatgttg gctagcgccg agagcttca  aaaggggaac  4080 gaactcgcac taccgtctaa atacgtgaat ttcctgtatt tagcgtccca ttacgagaag  4140
ttgaaaggtt cacctgaaga taacgaacag aagcaacttt tgttgagca  gcacaaacat  4200 tatctcgacg aaatcataga gcaaatttcg gaattcagta agagagtcat cctagctgat  4260
gccaatctgg acaaagtatt aagcgcatac aacaagcaca gggataaacc catacgtgag  4320
caggcggaaa atattatcca tttgtttact cttaccaacc tcggcgctcc agccgcattc  4380
aagtattttg acacaacgat agatcgcaaa cgatacactt ctaccaagga ggtgctagac  4440
gcgacactga ttcaccaatc catcacggga ttatatgaaa ctcggataga tttgtcacag  4500
cttgggggtg acggatcccc caagaagaag aggaaagtct cgagcgacta caaagaccat  4560
gacggtgatt ataaagatca tgacatcgat tacaaggatg acgatgacaa ggctgcagga  4620
ggcggtggaa gcgggcgcgc cgacgcgctg gacgatttcg atctcgacat gctgggttct  4680
gatgccctcg atgactttga cctggatatg ttgggaagcg acgcattgga tgactttgat  4740
ctggacatgc tcggctccga tgctctggac gatttcgatc tcgatatgtt ataaccggtc  4800
atcatcacca tcaccattga gtttaaaccc gctgatcagc ctcgactgtg ccttctagtt  4860
gccagccatc tgttgtttgc ccctcccccg tgccttcctt gaccctggaa ggtgccactc  4920
ccactgtcct ttcctaataa aatgaggaaa ttgcatcgca ttgtctgagt aggtgtcatt  4980
ctattctggg gggtggggtg ggcaggaca gcaaggggga ggattgggaa gacaatagca  5040
ggcatgctgg ggatgcggtg ggctctatgg cttctgaggc ggaaagaacc agctggggct  5100
cgataccgtc gacctctagc tagagcttgg cgtaatcatg gtcatagctg tttcctgtgt  5160
gaaattgtta tccgctcaca attccacaca acatacgagc cggaagcata aagtgtaaag  5220
cctagggtgc ctaatgagtg agctaactca cattaattgc gttgcgctca ctgcccgctt  5280
tccagtcggg aaacctgtcg tgccagctgc attaatgaat cggccaacgc gcgggagag  5340 gcggtttgcg tattgggcgc tcttccgctt cctcgctcac tgactcgctg cgctcggtcg  5400
ttcggctgcg gcgagcggta tcagctcact caaaggcggt aatacggtta tccacagaat  5460
caggggataa cgcaggaaag aacatgtgag caaaaggcca gcaaaaggcc aggaaccgta  5520
aaaaggccgc gttgctggcg ttttccata  ggctccgccc ccctgacgag catcacaaaa  5580
atcgacgctc aagtcagagg tggcgaaacc cgacaggact ataaagatac caggcgtttc  5640
cccctggaag ctccctcgtg cgctctcctg ttccgaccct gccgcttacc ggatacctgt  5700
ccgcctttct cccttcggga agcgtggcgc tttctcaatg ctcacgctgt aggtatctca  5760
gttcggtgta ggtcgttcgc tccaagctgg gctgtgtgca cgaaccccc  gttcagcccg  5820 accgctgcgc cttatccggt aactatcgtc ttgagtccaa cccggtaaga cacgacttat  5880
cgccactggc agcagccact ggtaacagga ttagcagagc gaggtatgta ggcggtgcta  5940
cagagttctt gaagtggtgg cctaactacg gctacactag aaggacagta tttggtatct  6000
gcgctctgct gaagccagtt accttcggaa aaagagttgg tagctcttga tccggcaaac  6060
aaaccaccgc tggtagcggt ggtttttttg tttgcaagca gcagattacg cgcagaaaaa  6120
aaggatctca agaagatcct ttgatctttt ctacggggtc tgacgctcag tggaacgaaa  6180
actcacgtta agggattttg gtcatgagat tatcaaaaag gatcttcacc tagatccttt  6240
taaattaaaa atgaagtttt aaatcaatct aaagtatata tgagtaaact tggtctgaca  6300
gttaccaatg cttaatcagt gaggcaccta tctcagcgat ctgtctattt cgttcatcca  6360
tagttgcctg actccccgtc gtgtagataa ctacgatacg ggagggctta ccatctggcc  6420
```

```
ccagtgctgc aatgataccg cgagacccac gctcaccggc tccagattta tcagcaataa    6480
accagccagc cggaagggcc gagcgcagaa gtggtcctgc aactttatcc gcctccatcc    6540
agtctattaa ttgttgccgg gaagctagag taagtagttc gccagttaat agtttgcgca    6600
acgttgttgc cattgctaca ggcatcgtgg tgtcacgctc gtcgtttggt atggcttcat    6660
tcagctccgg ttcccaacga tcaaggcgag ttacatgatc ccccatgttg tgcaaaaaag    6720
cggttagctc cttcggtcct ccgatcgttg tcagaagtaa gttggccgca gtgttatcac    6780
tcatggttat ggcagcactg cataattctc ttactgtcat gccatccgta agatgctttt    6840
ctgtgactgg tgagtactca accaagtcat tctgagaata gtgtatgcgg cgaccgagtt    6900
gctcttgccc ggcgtcaata cgggataata ccgcgccaca tagcagaact ttaaaagtgc    6960
tcatcattgg aaaacgttct cggggcgaaa actctcaag gatcttaccg ctgttgagat    7020
ccagttcgat gtaacccact cgtgcaccca actgatcttc agcatctttt actttcacca    7080
gcgtttctgg gtgagcaaaa acaggaaggc aaaatgccgc aaaaaaggga ataagggcga    7140
cacggaaatg ttgaatactc atactcttcc tttttcaata ttattgaagc atttatcagg    7200
gttattgtct catgagcgga tacatatttg aatgtattta gaaaaataaa caaatagggg    7260
ttccgcgcac atttccccga aaagtgccac ctgacgtcga cggatcggga gatcgatctc    7320
ccgatcccct agggtcgact ctcagtacaa tctgctctga tgccgcatag ttaagccagt    7380
atctgctccc tgcttgtgtg ttggaggtcg ctgagtagtg cgcgagcaaa atttaagcta    7440
caacaaggca aggcttgacc gacaattgca tgaagaatct gcttagggtt aggcgttttg    7500
cgctgcttcg cgatgtacgg gccagatata cgcgttgaca ttgattattg actagttatt    7560
aatagtaatc aattacgggg tcattagttc atagcccata tatggagttc cgcgttacat    7620
aacttacggt aaatggcccg cctggctgac cgcccaacga ccccgccca ttgacgtcaa    7680 taatgacgta tgttcccata gtaacgccaa tagggacttt ccattgacgt caatgggtgg    7740
actatttacg gtaaactgcc cacttggcag tacatcaagt gtatc                   7785
```

<210> SEQ ID NO 7
<211> LENGTH: 1452
<212> TYPE: PRT
<213> ORGANISM: Artificial Sequence
<220> FEATURE:
<223> OTHER INFORMATION: Cas9-activator protein sequence

<400> SEQUENCE: 7

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
```

115                 120                 125
His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960
```

-continued

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala Lys
            1010                1015                1020

Ser Glu Gln Glu Ile Gly Lys Ala Thr Ala Lys Tyr Phe Phe Tyr Ser
1025                1030                1035                1040

Asn Ile Met Asn Phe Phe Lys Thr Glu Ile Thr Leu Ala Asn Gly Glu
            1045                1050                1055

Ile Arg Lys Arg Pro Leu Ile Glu Thr Asn Gly Glu Thr Gly Glu Ile
            1060                1065                1070

Val Trp Asp Lys Gly Arg Asp Phe Ala Thr Val Arg Lys Val Leu Ser
            1075                1080                1085

Met Pro Gln Val Asn Ile Val Lys Lys Thr Glu Val Gln Thr Gly Gly
            1090                1095                1100

Phe Ser Lys Glu Ser Ile Leu Pro Lys Arg Asn Ser Asp Lys Leu Ile
1105                1110                1115                1120

Ala Arg Lys Lys Asp Trp Asp Pro Lys Lys Tyr Gly Gly Phe Asp Ser
            1125                1130                1135

Pro Thr Val Ala Tyr Ser Val Leu Val Val Ala Lys Val Glu Lys Gly
            1140                1145                1150

Lys Ser Lys Lys Leu Lys Ser Val Lys Glu Leu Leu Gly Ile Thr Ile
            1155                1160                1165

Met Glu Arg Ser Ser Phe Glu Lys Asn Pro Ile Asp Phe Leu Glu Ala
            1170                1175                1180

Lys Gly Tyr Lys Glu Val Lys Lys Asp Leu Ile Ile Lys Leu Pro Lys
1185                1190                1195                1200

Tyr Ser Leu Phe Glu Leu Glu Asn Gly Arg Lys Arg Met Leu Ala Ser
            1205                1210                1215

Ala Gly Glu Leu Gln Lys Gly Asn Glu Leu Ala Leu Pro Ser Lys Tyr
            1220                1225                1230

Val Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg Val
1265                1270                1275                1280

Ile Leu Ala Asp Ala Asn Leu Asp Lys Val Leu Ser Ala Tyr Asn Lys
            1285                1290                1295

His Arg Asp Lys Pro Ile Arg Glu Gln Ala Glu Asn Ile Ile His Leu
            1300                1305                1310

Phe Thr Leu Thr Asn Leu Gly Ala Pro Ala Ala Phe Lys Tyr Phe Asp
            1315                1320                1325

Thr Thr Ile Asp Arg Lys Arg Tyr Thr Ser Thr Lys Glu Val Leu Asp
            1330                1335                1340

Ala Thr Leu Ile His Gln Ser Ile Thr Gly Leu Tyr Glu Thr Arg Ile
1345                1350                1355                1360

Asp Leu Ser Gln Leu Gly Gly Asp Gly Ser Pro Tyr Lys Asp His Asp
            1365                1370                1375

Gly Asp Tyr Lys Asp His Asp Ile Asp Tyr Lys Asp Asp Asp Asp Lys

-continued

```
                      1380                1385                 1390
Ala Ala Gly Gly Gly Gly Ser Gly Arg Ala Asp Ala Leu Asp Asp Phe
                1395                1400                1405

Asp Leu Asp Met Leu Gly Ser Asp Ala Leu Asp Asp Phe Asp Leu Asp
        1410                1415                1420

Met Leu Gly Ser Asp Ala Leu Asp Asp Phe Asp Leu Asp Met Leu Gly
1425                1430                1435                1440

Ser Asp Ala Leu Asp Asp Phe Asp Leu Asp Met Leu
                1445                1450
```

RNA-GUIDED TARGETING OF GENETIC AND EPIGENOMIC REGULATORY PROTEINS TO SPECIFIC GENOMIC LOCI

CLAIM OF PRIORITY

This application claims priority under 35 USC § 119(e) to U.S. patent application Ser. No. 61/799,647, filed on Mar. 15, 2013. The entire contents of the foregoing are hereby incorporated by reference.

FEDERALLY SPONSORED RESEARCH OR DEVELOPMENT

This invention was made with Government support under Grant No. GM105378 awarded by the National Institutes of Health. The Government has certain rights in the invention.

TECHNICAL FIELD

This invention relates to methods and constructs for RNA-guided targeting of transcriptional activators to specific genomic loci.

BACKGROUND

Clustered Regulatory Interspaced Short Palindromic Repeats (CRISPR), and CRISPR-associated (cas) genes, referred to as CRISPR/Cas systems, are used by various bacteria and archaea to mediate defense against viruses and other foreign nucleic acid. These systems use small RNAs to detect and silence foreign nucleic acids in a sequence-specific manner.

Three types of CRISPR/Cas systems have been described (Makarova et al., Nat. Rev. Microbiol. 9, 467 (2011); Makarova et al., Biol. Direct 1, 7 (2006); Makarova et al., Biol. Direct 6, 38 (2011)). Recent work has shown that Type II CRISPR/Cas systems can be engineered to direct targeted double-stranded DNA breaks in vitro to specific sequences by using a single "guide RNA" with complementarity to the DNA target site and a Cas9 nuclease (Jinek et al., Science 2012; 337:816-821). This targetable Cas9-based system also works efficiently in cultured human cells (Mali et al., Science. 2013 Feb. 15; 339(6121):823-6; Cong et al., Science. 2013 Feb. 15; 339(6121):819-23) and in vivo in zebrafish (Hwang and Fu et al., Nat Biotechnol. 2013 March; 31(3): 227-9) for inducing targeted alterations into endogenous genes.

SUMMARY

At least in part, the present invention is based on the development of a fusion protein including a heterologous functional domain (a transcriptional activation domain) fused to a Cas9 nuclease that has had its nuclease activity inactivated by mutations. While published studies have used guide RNAs to target the Cas9 nuclease to specific genomic loci, no work has yet adapted this system to recruit additional effector domains. This work also provides the first demonstration of an RNA-guided process that results in an increase (rather than a decrease) in the level of expression of a target gene.

In addition, the present disclosure provides the first demonstration that multiplex gRNAs can be used to mediate synergistic activation of transcription.

Thus, in a first aspect, the invention provides fusion proteins comprising a catalytically inactive CRISPR associated 9 (Cas9) protein linked to a heterologous functional domain that modifies DNA, e.g., transcriptional activation domain, transcriptional repressors, enzymes that modify the methylation state of DNA (e.g., DNA methyltransferase (DNMT) or TET proteins), or enzymes that modify histone subunit (e.g., histone acetyltransferases (HAT), histone deacetylases (HDAC), or histone demethylases). In preferred embodiments, the heterologous functional domain is a transcriptional activation domain, e.g., a transcriptional activation domain is from VP64 or NF-κB p65.

In some embodiments, the catalytically inactive Cas9 protein is from *S. pyogenes*.

In some embodiments, the catalytically inactive Cas9 protein comprises mutations at D10A and H840A.

In some embodiments, the heterologous functional domain is linked to the N terminus or C terminus of the catalytically inactive Cas9 protein, with an optional intervening linker, wherein the linker does not interfere with activity of the fusion protein.

In some embodiments, the fusion protein includes one or both of a nuclear localization sequence and one or more epitope tags, e.g., c-myc, 6His, or FLAG tags, on the N-terminus, C-terminus, or in between the catalytically inactive CRISPR associated 9 (Cas9) protein and the heterologous functional domain, optionally with one or more intervening linkers.

In further aspect, the invention provides nucleic acid encoding the fusion proteins described herein, as well as expression vectors including the nucleic acids, and host cells expressing the fusion proteins.

In an additional aspect, the invention provides methods for increasing expression of a target gene in a cell. The methods include expressing a Cas9-activator fusion protein as described herein in the cell, e.g., by contacting the cell with an expression vector including a sequence encoding the fusion protein, and also expressing in the cell one or more guideRNAs directed to the target gene, e.g., by contacting the cell with one or more expression vectors comprising nucleic acid sequences encoding one or more guideRNAs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 4 is an exemplary sequence of a Guide RNA expression vector.

FIG. 5 is an exemplary sequence of CMV-T7-Cas9 D10A/H840A-3XFLAG-VP64.

FIG. 6 is an exemplary sequence of CMV-T7-Cas9 recoded D10A/H840A-3XFLAG-VP64.

FIG. 7 is an exemplary sequence of a Cas9-activator. An optional 3xFLAG sequence is underlined; the nuclear localization signal PKKKRKVS (SEQ ID NO:1) is in lower case; two linkers are in bold; and the VP64 transcriptional activator sequence, DALDDFDLDMLGSDALDDFDLDM-LGSDALDDFDLDMLGSDALDDFDLDML (SEQ ID NO:2), is boxed.

DETAILED DESCRIPTION

Described herein are fusion proteins of transcriptional activation domains fused to a catalytically inactivated version of the Cas9 protein for the purpose of enabling RNA-guided targeting of these functional domains to specific genomic locations in cells and living organisms.

The CRISPR/Cas system has evolved in bacteria as a defense mechanism to protect against invading plasmids and viruses. Short protospacers, derived from foreign nucleic acid, are incorporated into CRISPR loci and subsequently transcribed and processed into short CRISPR RNAs (crRNAs). These RNAs then use their sequence complementarity to the invading nucleic acid to guide Cas9-mediated cleavage, and consequent destruction of the foreign nucleic acid. Last year, Doudna and colleagues demonstrated that a single guide RNA (sgRNA) can mediate recruitment of Cas9 nuclease to specific DNA sequences in vitro (FIG. 1C; Jinek et al., Science 2012).

Figure 1A:
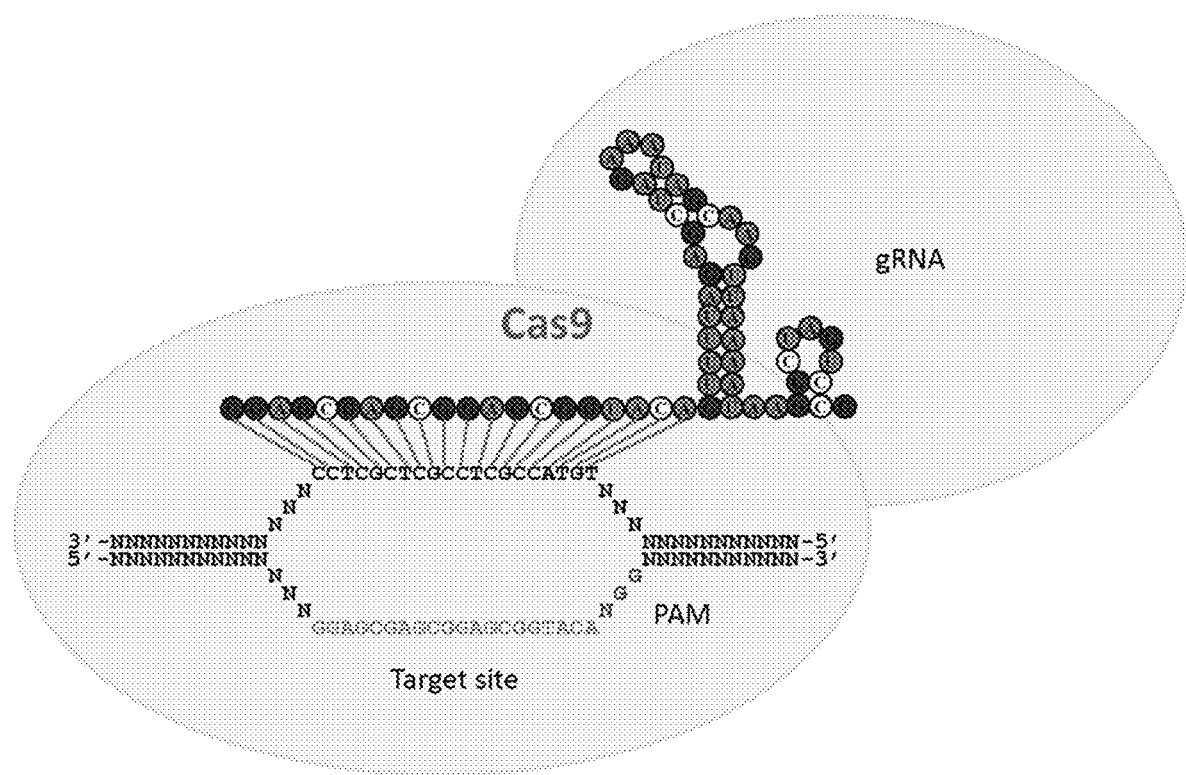
FIG. 1A is a schematic illustration showing a single guide RNA (sgRNA) recruiting Cas9 nuclease to a specific DNA sequence.
Figure 1B:
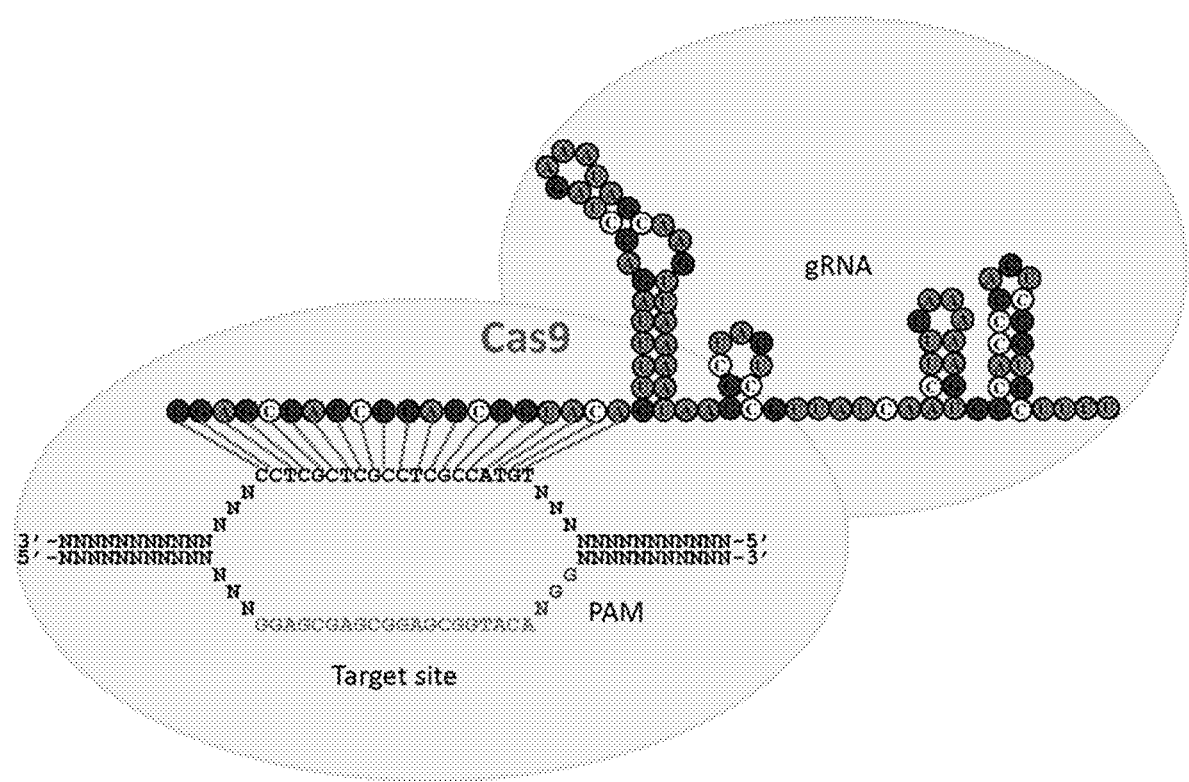
FIG. 1B is a schematic illustration showing a longer version of the sgRNA used to introduce targeted alterations.

More recently, a longer version of the sgRNA has been used to introduce targeted alterations in human cells and zebrafish (FIG. 1B; Mali et al. Science 2013, Hwang and Fu et al., Nat Biotechnol. 2013 March; 31(3):227-9).

Figure 1C:
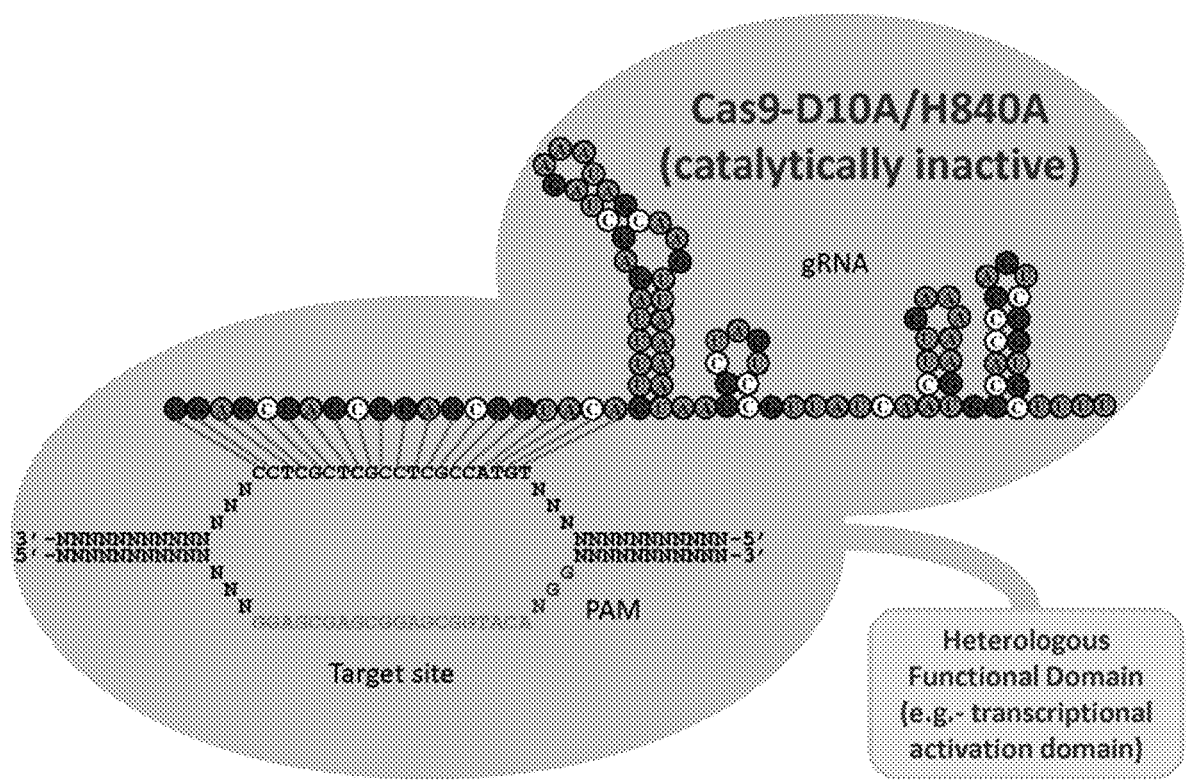
FIG. 1C is a schematic illustration showing a Cas9 protein containing D10A and H840A mutations to render the nuclease portion of the protein catalytically inactive fused to a transcriptional activation domain.

As described herein, in addition to guiding Cas9-mediated nuclease activity, it is possible to use CRISPR-derived RNAs to target heterologous functional domains fused to Cas9 to specific sites in the genome (FIG. 1C). As described herein, it is possible to use single guide RNAs (sgRNAs) to target Cas9-transcriptional activators (hereafter referred to as Cas9-activators) to the promoters of specific genes and thereby increase expression of the target gene. Cas9-activators can be localized to sites in the genome, with target specificity defined by sequence complementarity of the guide RNA.

In some embodiments, the present system utilizes the Cas9 protein from *S. pyogenes*, either as encoded in bacteria or codon-optimized for expression in mammalian cells, containing D10A and H840A mutations to render the nuclease portion of the protein catalytically inactive (FIG. 1C). The Cas9-activators are created by fusing a transcriptional activation domain, e.g., from either VP64 or NF-κB p65, to the N-terminus or C-terminus of the catalytically inactive Cas9 protein.

The sequence of the catalytically inactive Cas9 used herein is as follows; the mutations are in bold and underlined.

```
                                        (SEQ ID NO: 3)
            10         20         30         40
    MDKKYSIGLA IGTNSVGWAV ITDEYKVPSK KFKVLGNTDR 50         60         70         80
    HSIKKNLIGA LLFDSGETAE ATRLKRTARR RYTRRKNRIC 90        100        110        120
    YLQEIFSNEM AKVDDSFFHR LEESFLVEED KKHERHPIFG 130        140        150        160
    NIVDEVAYHE KYPTIYHLRK KLVDSTDKAD LRLIYLALAH 170        180        190        200
    MIKFRGHFLI EGDLNPDNSD VDKLFIQLVQ TYNQLFEENP 210        220        230        240
    INASGVDAKA ILSARLSKSR RLENLIAQLP GEKKNGLFGN 250        260        270        280
    LIALSLGLTP NFKSNFDLAE DAKLQLSKDT YDDDLDNLLA 290        300        310        320
    QIGDQYADLF LAAKNLSDAI LLSDILRVNT EITKAPLSAS 330        340        350        360
    MIKRYDEHHQ DLTLLKALVR QQLPEKYKEI FFDQSKNGYA 370        380        390        400
    GYIDGGASQE EFYKFIKPIL EKMDGTEELL VKLNREDLLR 410        420        430        440
    KQRTFDNGSI PHQIHLGELH AILRRQEDFY PFLKDNREKI 450        460        470        480
    EKILTFRIPY YVGPLARGNS RFAWMTRKSE ETITPWNFEE 490        500        510        520
    VVDKGASAQS FIERMTNFDK NLPNEKVLPK HSLLYEYFTV 530        540        550        560
    YNELTKVKYV TEGMRKPAFL SGEQKKAIVD LLFKTNRKVT 570        580        590        600
    VKQLKEDYFK KIECFDSVEI SGVEDRFNAS LGTYHDLLKI 610        620        630        640
    IKDKDFLDNE ENEDILEDIV LTLTLFEDRE MIEERLKTYA 650        660        670        680
    HLFDDKVMKQ LKRRRYTGWG RLSRKLINGI RDKQSGKTIL 690        700        710        720
    DFLKSDGFAN RNFMQLIHDD SLTFKEDIQK AQVSGQGDSL 730        740        750        760
    HEHIANLAGS PAIKKGILQT VKVVDELVKV MGRHKPENIV
```

-continued

```
          770         780         790         800
IEMARENQTT QKGQKNSRER MKRIEEGIKE LGSQILKEHP 810         820         830         840
VENTQLQNEK LYLYYLQNGR DMYVDQELDI NRLSDYDVDA 850         860         870         880
IVPQSFLKDD SIDNKVLTRS DKNRGKSDNV PSEEVVKKMK 890         900         910         920
NYWRQLLNAK LITQRKFDNL TKAERGGLSE LDKAGFIKRQ 930         940         950         960
LVETRQITKH VAQILDSRMN TKYDENDKLI REVKVITLKS 970         980         990        1000
KLVSDFRKDF QFYKVREINN YHHAHDAYLN AVVGTALIKK 1010        1020        1030        1040
YPKLESEFVY GDYKVYDVRK MIAKSEQEIG KATAKYFFYS 1050        1060        1070        1080
NIMNFFKTEI TLANGEIRKR PLIETNGETG EIVWDKGRDF 1090        1100        1110        1120
ATVRKVLSMP QVNIVKKTEV QTGGFSKESI LPKRNSDKLI 1130        1140        1150        1160
ARKKDWDPKK YGGFDSPTVA YSVLVVAKVE KGKSKKLKSV 1170        1180        1190        1200
KELLGITIME RSSFEKNPID FLEAKGYKEV KKDLIIKLPK 1210        1220        1230        1240
YSLFELENGR KRMLASAGEL QKGNELALPS KYVNFLYLAS 1250        1260        1270        1280
HYEKLKGSPE DNEQKQLFVE QHKHYLDEII EQISEFSKRV 1290        1300        1310        1320
ILADANLDKV LSAYNKHRDK PIREQAENII HLFTLTNLGA 1330        1340        1350        1360
PAAFKYFDTT IDRKRYTSTK EVLDATLIHQ SITGLYETRI

DLSQLGGD
```

The transcriptional activation domains can be fused on the N or C terminus of the Cas9. In addition, although the present description exemplifies transcriptional activation domains, other heterologous functional domains (e.g., transcriptional repressors, enzymes that modify the methylation state of DNA (e.g., DNA methyltransferase (DNMT) or TET proteins), or enzymes that modify histone subunit (e.g., histone acetyltransferases (HAT), histone deacetylases (HDAC), or histone demethylases)) as are known in the art can also be used. A number of sequences for such domains are known in the art, e.g., a domain that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
|---|---|---|
| Gene | Amino Acid | Nucleic Acid |
| TET1 | NP_085128.2 | NM_030625.2 |
| TET2* | NP_001120680.1 (var 1) | NM_001127208.2 |
| TET3 | NP_060098.3 (var 2) | NM_017628.4 |
| | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih.gov/pub/aravind/DONS/supplementary material DONS.html) for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

Methods of Use

The described Cas9-activator system is a useful and versatile tool for modifying the expression of endogenous genes. Current methods for achieving this require the generation of novel engineered DNA-binding proteins (such as engineered zinc finger or transcription activator-like effector DNA binding domains) for each site to be targeted. Because these methods demand expression of a large protein specifically engineered to bind each target site, they are limited in their capacity for multiplexing. Cas9-activators, however, require expression of only a single Cas9-activator protein, which can be targeted to multiple sites in the genome by expression of multiple short gRNAs. This system could therefore easily be used to simultaneously induce expression of a large number of genes. This capability will have broad utility, e.g., for basic biological research, where it can be used to study gene function and to manipulate the expression of multiple genes in a single pathway, and in synthetic biology, where it will enable researchers to create circuits in cell that are responsive to multiple input signals. The relative ease with which this technology can be implemented and adapted to multiplexing will make it a broadly useful technology with many wide-ranging applications.

The methods described herein include contacting cells with a nucleic acid encoding the Cas9-activators described herein, and nucleic acids encoding one or more guide RNAs directed to a selected gene, to thereby modulate expression of that gene. Guide RNAs, and methods of designing and expressing guide RNAs, are known in the art. See, e.g., Jinek et al., Science 2012; 337:816-821; Mali et al., Science. 2013 Feb. 15; 339(6121):823-6; Cong et al., Science. 2013 Feb. 15; 339(6121):819-23; and Hwang and Fu et al., Nat Biotechnol. 2013 March; 31(3):227-9). In some embodiments, the guideRNAs are directed to a region that is 100-800, e.g., about 500 bp upstream of the transcription start site. In some embodiments, vectors (e.g., plasmids) encoding more than one gRNA are used, e.g., plasmids encoding, 2, 3, 4, 5, or more gRNAs directed to different sites in the same region of the target gene.

Polypeptide Expression Systems

In order to use the fusion proteins described, it may be desirable to express the engineered proteins from a nucleic acid that encodes them. This can be performed in a variety of ways. For example, the nucleic acid encoding the fusion protein can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion protein or for production of the fusion protein. The nucleic acid encoding the fusion protein can also be cloned into an expression vector, for administration to a plant cell, animal cell, preferably a mammalian cell or a human cell, fungal cell, bacterial cell, or protozoan cell.

To obtain expression, the fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of the fusion protein nucleic acid depends on the particular application. For example, a strong constitutive promoter is typically used for expression and purification of fusion proteins. In contrast, when the fusion protein is to be administered in vivo for gene regulation, either a constitutive or an inducible promoter can be used, depending on the particular use of the fusion protein. In addition, a preferred promoter for administration of the fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the fusion protein, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ. A preferred tag-fusion protein is the maltose binding protein (MBP). Such tag-fusion proteins can be used for purification of the engineered TALE repeat protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include PMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101: 347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

In some embodiments, the fusion protein includes a nuclear localization domain which provides for the protein to be translocated to the nucleus. Several nuclear localization sequences (NLS) are known, and any suitable NLS can be used. For example, many NLSs have a plurality of basic amino acids, referred to as a bipartite basic repeats (reviewed in Garcia-Bustos et al, 1991, Biochim. Biophys. Acta, 1071:83-101). An NLS containing bipartite basic repeats can be placed in any portion of chimeric protein and results in the chimeric protein being localized inside the nucleus. In preferred embodiments a nuclear localization domain is incorporated into the final fusion protein, as the ultimate functions of the fusion proteins described herein will typically require the proteins to be localized in the nucleus. However, it may not be necessary to add a separate nuclear localization domain in cases where the DBD domain itself, or another functional domain within the final chimeric protein, has intrinsic nuclear translocation function.

The present invention includes the vectors and cells comprising the vectors.

EXAMPLES

The invention is further described in the following examples, which do not limit the scope of the invention described in the claims.

Example 1. Engineering CRISPR/Cas Activator System

To express guide RNAs (gRNAs) in human cells, we engineered a vector that would express the full length chimeric gRNA (a fusion of crRNA and tracrRNA originally described by Jinek et al. (Science 2012)) driven by a U6 promoter. To create site-specific gRNAs, a pair of 26 nucleotide oligos are annealed and ligated into the BsmBI-digested vector backbone. See FIG. 4.

To engineer a Cas9-activator we introduced the D10A, H840A catalytic mutations (previously described in Jinek et al. Science 2012)) into either the wildtype or a codon-optimized Cas9 sequence (FIG. 5). These mutations render the Cas9 catalytically inactive so that it will no longer induce double-strand breaks. In one construct, a triple flag tag, nuclear localization signal and the VP64 activation domain were fused to the C-terminus of the inactive Cas9 (FIG. 6). Expression of this fusion protein is driven by the CMV promoter.

Cell Culture, Transfection and ELISA Assays were Performed as Follows.

Flp-In T-Rex 293 cells were maintained in Advanced DMEM supplemented with 10% FBS, 1% penstrep and 1% Glutamax (Invitrogen). Cells were transfected by Lipofectamine LTX (Invitrogen) according to manufacturer's instructions. Briefly, 160,000 293 cells were seeded in 24-well plates and transfected the following day with 250 ng gRNA plasmid, 250 ng Cas9-VP64 plasmid, 30 ng GFP, 0.5 ul Plus Reagent and 1.65 ul Lipofectamine LTX. Tissue culture media from transfected 293 cells was harvested 40 hours after transfection, and secreted VEGF-A protein assayed using R&D System's Human VEGF-A ELISA kit "Human VEGF Immunoassay."

Figure 2:
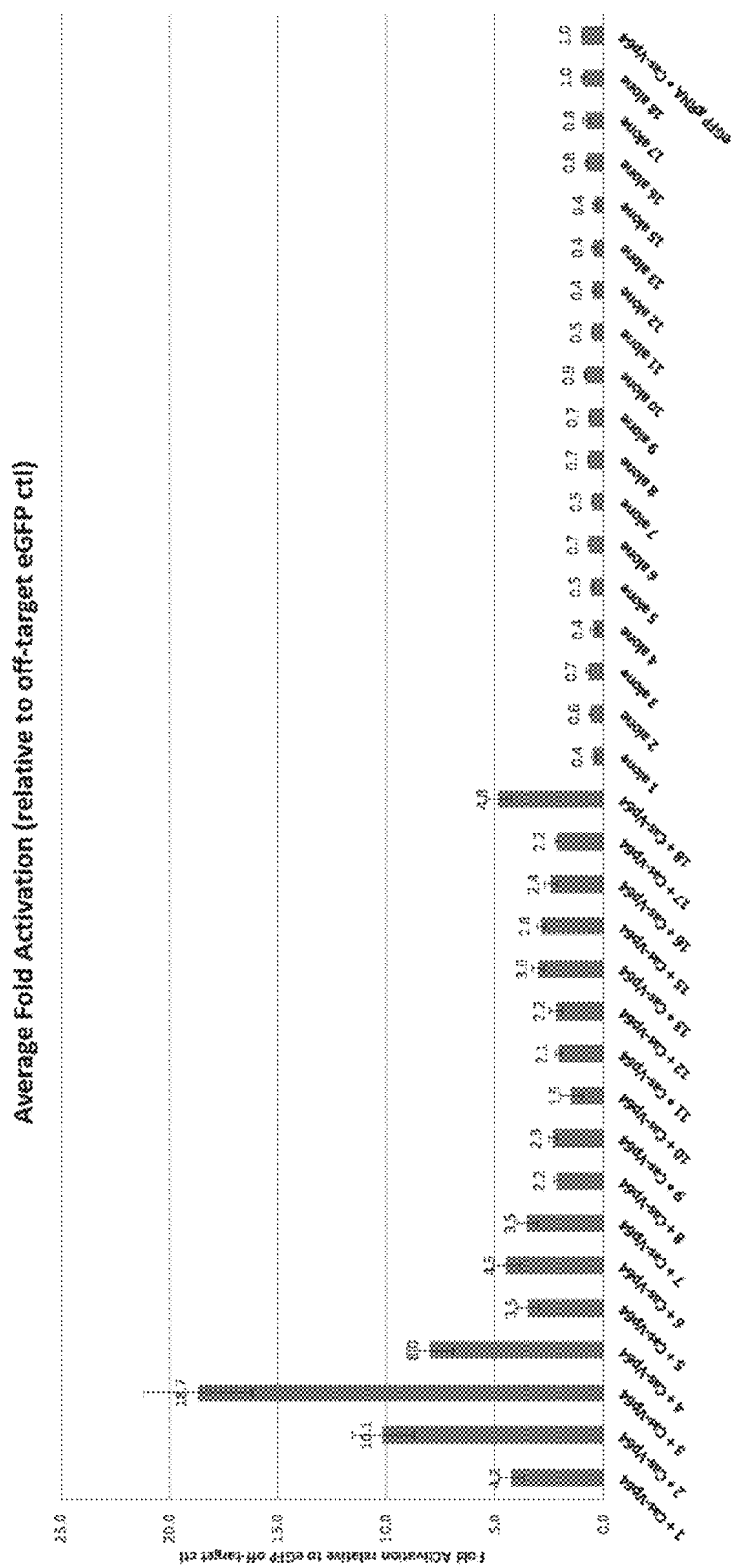
FIG. 2 is a bar graph showing levels of VEGFA protein expression in cells transfected with gRNA and Cas9-VP64. Fold activation was calculated relative to off-target gRNA control. Error bars represent standard error of the mean of three independent replicates. 1–18=18 guide RNAs targeted to various sites in the human VEGF-A gene; Cas9-Vp64=Fusion of catalytically inactive Cas9 (bearing D10A/H840A mutations) fused to the VP64 Activation domain; eGFP gRNA=a guide RNA targeted to an off-target site located in an EGFP Reporter gene

17 gRNAs were engineered to target three different regions (−500, 0 and +500 bp relative to the start site of transcription) in the human VEGFA promoter. Each gRNA was cotransfected with Cas9-VP64 into Hek293 cells and expression levels of VEGF-A protein was measured by ELISA. Of the 17 gRNAs, nine increased expression of VEGFA by three-fold or more as compared to an off-target gRNA control (FIG. 2). The greatest increase in VEGFA was observed in cells transfected with gRNA3, which induced protein expression by 18.7-fold. Interestingly, the three best gRNAs, and 6 of the 9 gRNAs capable of inducing expression by 3-fold or more, target the −500 region (~500 bp upstream of the transcription start site).

Figure 3A:
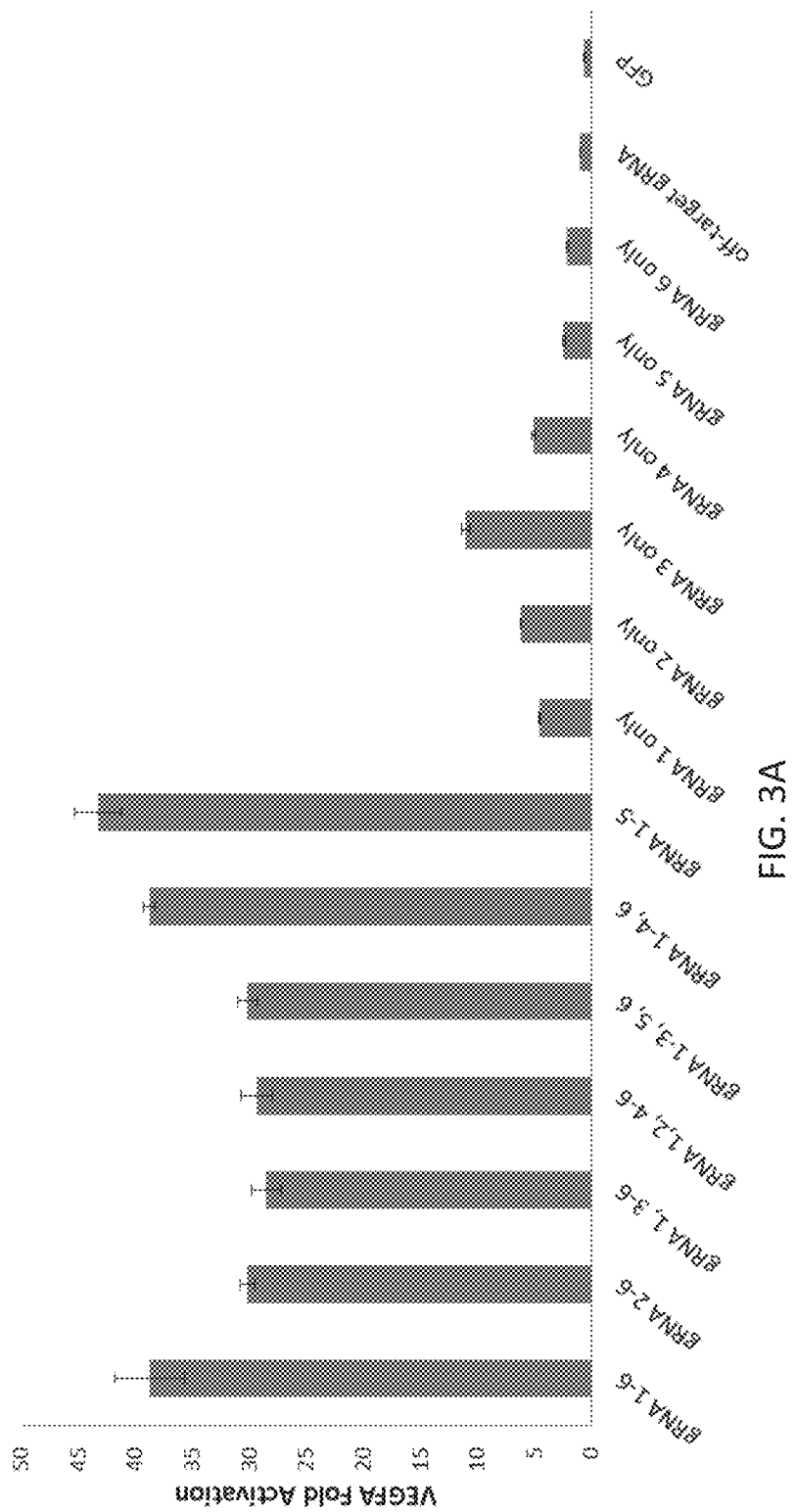
FIG. 3A is a bar graph showing VEGFA protein expression in cells transfected with multiple gRNAs and Cas9-VP64, demonstrating synergistic activation of VEGFA. Fold activation was calculated relative to off-target gRNA control. Error bars represent standard error of the mean of three independent replicates.
Figure 3B:
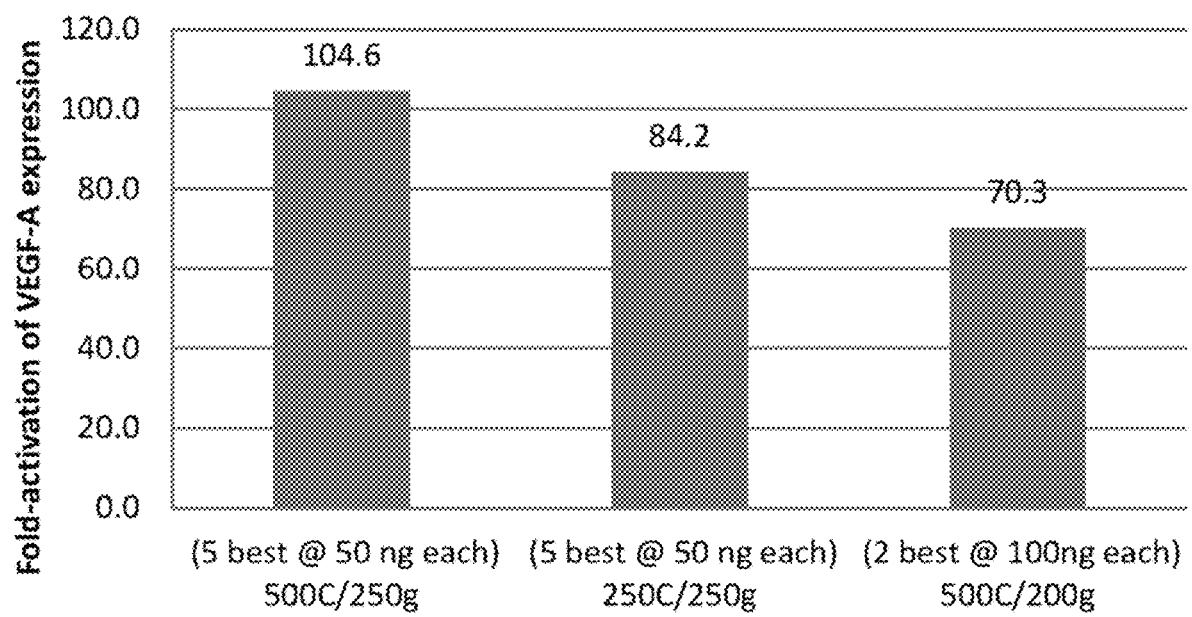
FIG. 3B is a bar graph showing VEGFA protein expression in cells transfected with multiple gRNAs and Cas9-VP64. The number underneath each bar indicate the amount in nanograms (ng) of Cas-activator (C) plasmid or guide RNA (g) plasmid transfected.

Plasmids encoding one, or more, e.g., two or five, different guide RNAs targeted to the human VEGFA promoter were transfected together with a plasmid encoding the Cas9-activator and assessed for their abilities to activate transcription of the VEGFA promoter. Combinations of multiple gRNAs further increased the level of VEGFA activation (FIGS. 3A-B). Co-transfection of all 6 gRNAs targeted to the −500 region and all possible combinations of 5 of these 6 gRNAs resulted in a synergistic increase in VEGFA protein expression (FIG. 3A).

These experiments demonstrate that co-expression of a Cas9-activator protein (harboring the VP64 transcriptional activation domain) and a gRNA with 20 nt of sequence complementarity to sites in the human VEGF-A promoter in human HEK293 cells can result in upregulation of VEGF-A expression. Increases in VEGF-A protein were measured by ELISA assay and it was found that individual gRNAs can function together with a Cas9-activator fusion protein to increase VEGF-A protein levels by up to ~18-fold (FIG. 2). Additionally, it was possible to achieve even greater increases in activation through transcriptional synergy by introducing multiple gRNAs targeting various sites in the same promoter together with Cas9-activator fusion proteins (FIGS. 3A-B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of increasing expression of a target gene in a mammalian cell, the method comprising contacting the mammalian cell in vitro with an expression vector comprising a promoter operably linked to a nucleic acid encoding a fusion protein comprising a catalytically inactive *S. pyogenes* CRISPR associated 9 (Cas9) protein linked to a heterologous functional domain, and one or more expression vectors comprising a promoter operably linked to nucleic acid sequences encoding one or more guideRNAs directed to a promoter of the target gene, wherein the catalytically inactive Cas9 protein comprises mutations at D10 and H840, and the heterologous functional domain is a transcriptional activation domain, wherein the contacted mammalian cell expresses the Cas9 fusion protein and the one or more guideRNAs such that the expressed Cas9 fusion protein is directed to the promoter of the target gene by the expressed one or more guideRNAs, and wherein the transcriptional activation domain mediates the increased expression.

2. A method of increasing expression of a target gene in a mammalian cell in vitro, the method comprising expressing in the mammalian cell a fusion protein comprising a catalytically inactive *S. pyogenes* Cas9 protein linked to a heterologous functional domain, and expressing one or more guideRNAs directed to the target gene, wherein the catalytically inactive Cas9 protein comprises mutations at D10 and H840, and the heterologous functional domain is a transcriptional activation domain, wherein the expressed Cas9 fusion protein is directed to the target gene by the one or more guideRNAs, and wherein the transcriptional activation domain mediates the increased expression.

3. The method of claim 2, wherein the transcriptional activation domain is a transcriptional activation domain selected from the group consisting of VP64 and NF-κB p65.

4. The method of claim 2, wherein the heterologous functional domain is linked to the N terminus or the C terminus of the catalytically inactive Cas9 protein, with an optional intervening linker, wherein the linker does not interfere with activity of the fusion protein.

5. The method of claim 2, further comprising one or both of a nuclear localization sequence and one or more epitope tags on the N-terminus, the C-terminus, or in between the catalytically inactive Cas9 protein and the heterologous functional domain, optionally with one or more intervening linkers.

6. The method of claim 5, wherein the one or more epitope tags is selected from the group consisting of c-myc, 6His, and FLAG tags.

7. The method of claim 2, wherein expressing the fusion protein in the mammalian cell comprises contacting the mammalian cell with an expression vector comprising a promoter operably linked to a nucleic acid encoding the fusion protein.

8. The method of claim 2, wherein expressing the one or more guideRNAs directed to the target gene in the mammalian cell comprises contacting the mammalian cell with one or more expression vectors comprising a promoter operably linked to nucleic acid sequences encoding the one or more guideRNAs directed to the target gene.

9. A method of increasing expression of a target gene in a mammalian cell in vitro, the method comprising expressing in the mammalian cell a fusion protein comprising a catalytically inactive *S. pyogenes* Cas9 protein linked to a transcriptional activation domain, and expressing one or more guideRNAs directed to the target gene, wherein the catalytically inactive Cas9 protein comprises mutations at D10 and H840, and the transcriptional activation domain is an enzyme that modifies the methylation state of DNA, and wherein the expressed Cas9 fusion protein is directed to the target gene by the one or more guideRNAs, wherein the transcriptional activation domain mediates the increased expression.

10. The method of claim 9, wherein the transcriptional activation domain is linked to the N terminus or the C terminus of the catalytically inactive Cas9 protein, with an optional intervening linker, wherein the linker does not interfere with activity of the fusion protein.

11. The method of claim 9, further comprising one or both of a nuclear localization sequence and one or more epitope tags on the N-terminus, the C-terminus, or in between the catalytically inactive Cas9 protein and the transcriptional activation domain, optionally with one or more intervening linkers.

12. The method of claim 11, wherein the one or more epitope tags is selected from the group consisting of c-myc, 6His, and FLAG tags.

13. The method of claim 9, wherein expressing the fusion protein in the mammalian cell comprises contacting the mammalian cell with an expression vector comprising a promoter operably linked to a nucleic acid encoding the fusion protein.

14. The method of claim 9, wherein expressing the one or more guideRNAs directed to the target gene in the mammalian cell comprises contacting the mammalian cell with one or more expression vectors comprising a promoter operably linked to nucleic acid sequences encoding the one or more guideRNAs directed to the target gene.

15. A method of increasing expression of a target gene in a mammalian cell in vitro, the method comprising expressing in the mammalian cell a fusion protein comprising a catalytically inactive *S. pyogenes* Cas9 protein linked to a transcriptional activation domain, and expressing one or more guideRNAs directed to the target gene, wherein the catalytically inactive Cas9 protein comprises mutations at D10 and H840, and the transcriptional activation domain is an enzyme that modifies histones, and wherein the expressed Cas9 fusion protein is directed to the target gene by the one or more guideRNAs, wherein the transcriptional activation domain mediates the increased expression.

16. The method of claim 15, wherein the transcriptional activation domain is linked to the N terminus or the C terminus of the catalytically inactive Cas9 protein, with an optional intervening linker, wherein the linker does not interfere with activity of the fusion protein.

17. The method of claim 15, further comprising one or both of a nuclear localization sequence and one or more epitope tags on the N-terminus, the C-terminus, or in between the catalytically inactive Cas9 protein and the transcriptional activation domain, optionally with one or more intervening linkers.

18. The method of claim 17, wherein the one or more epitope tags is selected from the group consisting of c-myc, 6His, and FLAG tags.

19. The method of claim 15, wherein expressing the fusion protein in the mammalian cell comprises contacting the mammalian cell with an expression vector comprising a promoter operably linked to a nucleic acid encoding the fusion protein.

20. The method of claim 15, wherein expressing the one or more guideRNAs directed to the target gene in the mammalian cell comprises contacting the mammalian cell with one or more expression vectors comprising a promoter operably linked to nucleic acid sequences encoding the one or more guideRNAs directed to the target gene.

\* \* \* \* \*